(12) United States Patent
Xie et al.

(10) Patent No.: US 12,411,125 B2
(45) Date of Patent: Sep. 9, 2025

(54) NANOPORE SENSING DEVICE

(71) Applicant: Oxford Nanopore Technologies PLC, Oxford (GB)

(72) Inventors: Ping Xie, Oxford (GB); Justin Millis, Oxford (GB); Rhodri Davies, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 138 days.

(21) Appl. No.: 18/016,012

(22) PCT Filed: Jul. 14, 2021

(86) PCT No.: PCT/GB2021/051806
§ 371 (c)(1),
(2) Date: Jan. 13, 2023

(87) PCT Pub. No.: WO2022/013551
PCT Pub. Date: Jan. 20, 2022

(65) Prior Publication Data
US 2023/0349882 A1    Nov. 2, 2023

Related U.S. Application Data

(60) Provisional application No. 63/053,122, filed on Jul. 17, 2020.

(51) Int. Cl.
*G01N 33/487*    (2006.01)
(52) U.S. Cl.
CPC .............................. *G01N 33/48721* (2013.01)

(58) Field of Classification Search
None
See application file for complete search history.

(56) References Cited

U.S. PATENT DOCUMENTS

| 3,799,743 | A | 3/1974 | Alexander et al. |
| 4,154,795 | A | 5/1979 | Thorne |
| 4,874,500 | A | 10/1989 | Madou et al. |

(Continued)

FOREIGN PATENT DOCUMENTS

| AU | 2003240941 A1 | 12/2003 |
| CN | 1303147 A | 7/2001 |

(Continued)

OTHER PUBLICATIONS

International Search Report and Written Opinion for Application No. PCT/GB2021/051806, mailed Sep. 28, 2021.

(Continued)

*Primary Examiner* — J. Christopher Ball
(74) *Attorney, Agent, or Firm* — Wolf, Greenfield & Sacks, P.C.

(57) ABSTRACT

A nanopore sensing device comprises a planar structure provided with plural fluidic passages extending between the first and second chambers. The planar structure supports nanopores in membranes across respective passages and sensor electrodes are arranged to sense a fluidic electrical potential in respective passages between the nanopores and the second chamber. The passages comprise planar fluidic resistor portions between the sensor electrode and the second chamber, the planar fluidic resistor portions extending in a planar direction of the planar structure and being configured to form a fluidic resistor.

30 Claims, 9 Drawing Sheets

(56) References Cited

U.S. PATENT DOCUMENTS

| | | |
|---|---|---|
| 5,234,566 A | 8/1993 | Osman et al. |
| 5,290,240 A | 3/1994 | Horres, Jr. |
| 5,403,451 A | 4/1995 | Riviello et al. |
| 5,503,803 A | 4/1996 | Brown et al. |
| 6,056,922 A | 5/2000 | Ikematsu |
| 6,300,141 B1 | 10/2001 | Segal et al. |
| 6,479,288 B1 | 11/2002 | Laffafian et al. |
| 6,483,931 B2 | 11/2002 | Kalnitsky et al. |
| 6,503,452 B1 | 1/2003 | Boxer et al. |
| 6,699,697 B2 | 3/2004 | Klemic et al. |
| 6,863,833 B1 | 3/2005 | Bloom et al. |
| 6,913,697 B2 | 7/2005 | Lopez et al. |
| 6,916,488 B1 | 7/2005 | Meier et al. |
| 7,077,939 B1 | 7/2006 | Crooks et al. |
| 7,144,486 B1 | 12/2006 | Fritsch et al. |
| 7,169,272 B2 | 1/2007 | Fritsch et al. |
| 7,294,247 B1 | 11/2007 | Tian et al. |
| 7,745,116 B2 | 6/2010 | Williams |
| 7,939,270 B2 | 5/2011 | Holden et al. |
| 8,124,191 B2 | 2/2012 | Ervin et al. |
| 8,197,775 B2 | 6/2012 | Johnston et al. |
| 8,461,854 B2 | 6/2013 | Chen et al. |
| 9,057,102 B2 | 6/2015 | Turner et al. |
| 9,546,400 B2 | 1/2017 | Turner et al. |
| 9,556,480 B2 | 1/2017 | Turner et al. |
| 9,613,247 B2 | 4/2017 | Yang |
| 9,678,056 B2 | 6/2017 | Turner et al. |
| 9,734,382 B2 | 8/2017 | Wang et al. |
| 9,738,929 B2 | 8/2017 | Turner et al. |
| 9,927,398 B2 | 3/2018 | Reid et al. |
| 10,036,065 B2 | 7/2018 | Jones |
| 10,215,768 B2 | 2/2019 | Sanghera et al. |
| 10,338,056 B2 | 7/2019 | Hyde et al. |
| 10,416,117 B2 | 9/2019 | Reid et al. |
| 10,549,274 B2 | 2/2020 | Brown et al. |
| 10,814,298 B2 | 10/2020 | Hyde et al. |
| 11,084,015 B2 | 8/2021 | Hyde et al. |
| 11,097,269 B2 | 8/2021 | Goto et al. |
| 11,561,216 B2 | 1/2023 | Hyde et al. |
| 11,596,940 B2 | 3/2023 | Waterman |
| 11,789,006 B2 | 10/2023 | Xie et al. |
| 11,913,936 B2 | 2/2024 | Hyde et al. |
| 12,121,894 B2 | 10/2024 | Waterman |
| 12,140,563 B2 | 11/2024 | Reid et al. |
| 2002/0074227 A1 | 6/2002 | Nisch et al. |
| 2002/0123048 A1 | 9/2002 | Gau |
| 2002/0144905 A1 | 10/2002 | Schmidt |
| 2003/0015422 A1 | 1/2003 | Fritsch et al. |
| 2003/0075445 A1 | 4/2003 | Woudenberg et al. |
| 2003/0098248 A1 | 5/2003 | Vogel et al. |
| 2003/0111340 A1 | 6/2003 | Cheng et al. |
| 2003/0148401 A1 | 8/2003 | Agrawal et al. |
| 2003/0224523 A1 | 12/2003 | Thornberg et al. |
| 2004/0022677 A1 | 2/2004 | Wohlstadter et al. |
| 2004/0096358 A1 | 5/2004 | Blankstein et al. |
| 2004/0171169 A1 | 9/2004 | Kallury et al. |
| 2005/0014162 A1 | 1/2005 | Barth et al. |
| 2005/0133101 A1 | 6/2005 | Chung et al. |
| 2005/0230272 A1 | 10/2005 | Lee et al. |
| 2005/0279634 A1 | 12/2005 | Ozaki et al. |
| 2006/0079009 A1 | 4/2006 | Salmon et al. |
| 2006/0163063 A1 | 7/2006 | Picollet-Dahan et al. |
| 2006/0194331 A1 | 8/2006 | Pamula et al. |
| 2006/0257941 A1 | 11/2006 | McDevitt et al. |
| 2006/0257992 A1 | 11/2006 | McDevitt et al. |
| 2006/0292649 A1 | 12/2006 | Cahill et al. |
| 2007/0035308 A1 | 2/2007 | Ide |
| 2007/0161101 A1 | 7/2007 | Takeuchi |
| 2007/0275480 A1 | 11/2007 | Brander et al. |
| 2008/0254995 A1 | 10/2008 | Kim et al. |
| 2009/0072332 A1 | 3/2009 | Dekker et al. |
| 2009/0142504 A1 | 6/2009 | Ervin et al. |
| 2009/0167288 A1 | 7/2009 | Reid et al. |
| 2009/0185955 A1 | 7/2009 | Nellisen |
| 2010/0035349 A1 | 2/2010 | Bau et al. |
| 2010/0147450 A1 | 6/2010 | Takeuchi et al. |
| 2010/0188109 A1 | 7/2010 | Edel et al. |
| 2010/0190253 A1 | 7/2010 | Tazaki et al. |
| 2010/0196203 A1 | 8/2010 | Sanghera et al. |
| 2010/0264935 A1 | 10/2010 | Erdman et al. |
| 2010/0304980 A1 | 12/2010 | Takeuchi et al. |
| 2011/0043234 A1 | 2/2011 | Lee et al. |
| 2011/0120871 A1 | 5/2011 | Reid et al. |
| 2011/0121840 A1 | 5/2011 | Sanghera et al. |
| 2011/0133255 A1 | 6/2011 | Merz |
| 2011/0214991 A1 | 9/2011 | Kim et al. |
| 2011/0274737 A1 | 11/2011 | Palmaz |
| 2011/0287414 A1 | 11/2011 | Chen et al. |
| 2011/0318774 A1 | 12/2011 | Larsen |
| 2012/0010085 A1 | 1/2012 | Rava et al. |
| 2013/0048499 A1 | 2/2013 | Mayer et al. |
| 2013/0071932 A1 | 3/2013 | Itchoda et al. |
| 2013/0140192 A1 | 6/2013 | Behrends et al. |
| 2013/0196442 A1 | 8/2013 | Momose et al. |
| 2013/0207205 A1 | 8/2013 | Chen |
| 2013/0217106 A1 | 8/2013 | Jones et al. |
| 2013/0270521 A1 | 10/2013 | Peng et al. |
| 2013/0309776 A1 | 11/2013 | Drndic et al. |
| 2014/0010735 A1 | 1/2014 | Tanaka et al. |
| 2014/0174927 A1 | 6/2014 | Bashir et al. |
| 2014/0190833 A1 | 7/2014 | Lieber et al. |
| 2014/0243214 A1 | 8/2014 | Haga et al. |
| 2014/0255921 A1 | 9/2014 | Moysey et al. |
| 2014/0296083 A1 | 10/2014 | Brown et al. |
| 2014/0318964 A1 | 10/2014 | Dunbar et al. |
| 2014/0329693 A1 | 11/2014 | Reid et al. |
| 2014/0335512 A1 | 11/2014 | Moysey et al. |
| 2014/0346059 A1 | 11/2014 | Akeson |
| 2014/0346515 A1 | 11/2014 | Yanagi et al. |
| 2014/0371568 A1 | 12/2014 | Selby et al. |
| 2015/0014160 A1 | 1/2015 | Hyde et al. |
| 2015/0027885 A1 | 1/2015 | Rajaraman et al. |
| 2015/0028846 A1 | 1/2015 | Zhu |
| 2015/0065354 A1 | 3/2015 | Moysey et al. |
| 2015/0151295 A1 | 6/2015 | Kimura et al. |
| 2015/0191709 A1 | 7/2015 | Heron et al. |
| 2015/0198611 A1 | 7/2015 | Ostrowski et al. |
| 2015/0204763 A1 | 7/2015 | Stelzle et al. |
| 2015/0218629 A1 | 8/2015 | Heron et al. |
| 2015/0232923 A1 | 8/2015 | Drndic et al. |
| 2015/0259724 A1 | 9/2015 | Guan et al. |
| 2015/0265994 A1 | 9/2015 | Hyde et al. |
| 2015/0268256 A1 | 9/2015 | Sanghera et al. |
| 2015/0300986 A1 | 10/2015 | Reid et al. |
| 2016/0040230 A1 | 2/2016 | Akeson |
| 2016/0178576 A1 | 6/2016 | Maney et al. |
| 2016/0231307 A1 | 8/2016 | Xie |
| 2016/0257942 A1 | 9/2016 | Bruce et al. |
| 2017/0189906 A1 | 7/2017 | Moll et al. |
| 2017/0326550 A1 | 11/2017 | Brown et al. |
| 2017/0363577 A1 | 12/2017 | Reid et al. |
| 2018/0321188 A1 | 11/2018 | Reid et al. |
| 2018/0372713 A1 | 12/2018 | Stamm et al. |
| 2019/0210021 A1 | 7/2019 | Waterman |
| 2019/0242913 A1 | 8/2019 | Sanghera et al. |
| 2019/0391128 A1 | 12/2019 | Hyde et al. |
| 2020/0292521 A1 | 9/2020 | Xie et al. |
| 2021/0086160 A1 | 3/2021 | Hyde et al. |
| 2021/0170403 A1 | 6/2021 | Waterman |
| 2021/0300750 A1 | 9/2021 | Waterman |
| 2022/0023819 A1 | 1/2022 | Hyde et al. |
| 2023/0228733 A1 | 7/2023 | Hyde et al. |
| 2023/0258592 A1 | 8/2023 | Bedau |
| 2023/0311118 A1 | 10/2023 | Waterman |
| 2024/0069007 A1 | 2/2024 | Xie et al. |
| 2024/0369531 A1 | 11/2024 | Hyde et al. |
| 2025/0033016 A1 | 1/2025 | Hyde et al. |
| 2025/0073708 A1 | 3/2025 | Waterman |
| 2025/0093296 A1 | 3/2025 | Reid et al. |

FOREIGN PATENT DOCUMENTS

| | | |
|---|---|---|
| CN | 1434461 | 8/2003 |
| CN | 1500555 A | 6/2004 |

(56) References Cited

FOREIGN PATENT DOCUMENTS

| | | |
|---|---|---|
| CN | 101078704 | 11/2007 |
| CN | 100448007 C | 12/2008 |
| CN | 101490277 A | 7/2009 |
| CN | 100571871 C | 12/2009 |
| CN | 102263104 A | 11/2011 |
| CN | 203466320 U | 9/2013 |
| CN | 103370617 A | 10/2013 |
| CN | 103995035 A | 8/2014 |
| CN | 205828393 U | 12/2016 |
| CN | 106457247 A | 2/2017 |
| DE | 102010022929 A1 | 12/2011 |
| EP | 0532215 A2 | 3/1993 |
| EP | 1110084 A1 | 6/2001 |
| EP | 1120469 A2 | 8/2001 |
| EP | 1419818 A1 | 5/2004 |
| EP | 1535667 A1 | 6/2005 |
| EP | 1669746 A1 | 6/2006 |
| EP | 1677102 | 7/2006 |
| EP | 1688742 | 8/2006 |
| EP | 1710578 | 10/2006 |
| EP | 1712909 A1 | 10/2006 |
| EP | 1779921 A1 | 5/2007 |
| EP | 2219032 A1 | 8/2010 |
| GB | 2237390 | 5/1991 |
| GB | 2446823 | 8/2008 |
| JP | S5-274882 A | 6/1977 |
| JP | 4014773 A2 | 1/1992 |
| JP | 4127066 B2 | 4/1992 |
| JP | H04-215052 A | 8/1992 |
| JP | 7307172 A2 | 11/1995 |
| JP | 2004-158330 A2 | 6/2004 |
| JP | 2005-098718 | 4/2005 |
| JP | 2005-164276 A | 6/2005 |
| JP | 2005-300460 A | 10/2005 |
| JP | 2005-539242 A | 12/2005 |
| JP | 2006-312141 A | 11/2006 |
| JP | 2008-194573 A | 8/2008 |
| JP | 2009-128206 A | 6/2009 |
| JP | 2010-186677 A2 | 8/2010 |
| JP | 2012-247231 A | 12/2012 |
| JP | 2013-148425 A | 8/2013 |
| JP | 2013-242247 A | 12/2013 |
| JP | 2014-190891 A | 10/2014 |
| JP | 2014-529296 A | 11/2014 |
| JP | 2015-064373 A | 4/2015 |
| JP | 2018-510329 A | 4/2018 |
| KR | 10-2017-0012367 | 2/2017 |
| WO | WO 1988/008534 A1 | 11/1988 |
| WO | WO 1994/025862 A1 | 11/1994 |
| WO | WO 1997/016545 A1 | 5/1997 |
| WO | WO 1998/058248 | 12/1998 |
| WO | WO 1999/013101 A1 | 3/1999 |
| WO | WO 2000/013014 A1 | 3/2000 |
| WO | WO 2000/025121 A1 | 5/2000 |
| WO | WO 2000/028312 | 5/2000 |
| WO | WO 2001/059447 A1 | 8/2001 |
| WO | WO 2002/024862 A2 | 3/2002 |
| WO | WO 2002/029402 A2 | 4/2002 |
| WO | WO 2002/035221 A1 | 5/2002 |
| WO | WO 2002/082046 A2 | 10/2002 |
| WO | WO 2003/052420 A2 | 6/2003 |
| WO | WO 2005/040783 A1 | 5/2005 |
| WO | WO 2005/124888 A1 | 12/2005 |
| WO | WO 2006/012571 A1 | 2/2006 |
| WO | WO 2006/076703 A2 | 7/2006 |
| WO | WO 2006/100484 | 9/2006 |
| WO | WO 2006/104639 | 10/2006 |
| WO | WO 2006/113550 | 10/2006 |
| WO | WO 2006/138160 A2 | 12/2006 |
| WO | WO 2007/028003 A2 | 3/2007 |
| WO | WO 2007/049576 A1 | 5/2007 |
| WO | WO 2007/116978 A1 | 10/2007 |
| WO | WO 2007/127327 | 11/2007 |
| WO | WO 2007/132002 A1 | 11/2007 |
| WO | WO 2008/012552 A1 | 1/2008 |
| WO | WO 2008/054611 A2 | 5/2008 |
| WO | WO 2008/102120 | 8/2008 |
| WO | WO 2008/102121 | 8/2008 |
| WO | WO 2008/124107 A1 | 10/2008 |
| WO | WO 2008/137008 A2 | 11/2008 |
| WO | WO 2008/156041 A1 | 12/2008 |
| WO | WO 2009/024775 A1 | 2/2009 |
| WO | WO 2009/035647 A1 | 3/2009 |
| WO | WO 2009/077734 A2 | 6/2009 |
| WO | WO 2010/086603 A1 | 8/2010 |
| WO | WO 2010/122293 | 10/2010 |
| WO | WO 2010/142954 A1 | 12/2010 |
| WO | WO 2011/046706 A1 | 4/2011 |
| WO | WO 2011/067559 A1 | 6/2011 |
| WO | WO 2011/118211 A1 | 9/2011 |
| WO | WO 2011/154114 A2 | 12/2011 |
| WO | WO 2012/033524 A2 | 3/2012 |
| WO | WO 2012/042226 A2 | 4/2012 |
| WO | WO 2012/107778 A2 | 8/2012 |
| WO | WO 2012/138357 A1 | 10/2012 |
| WO | WO 2013/012881 A2 | 1/2013 |
| WO | WO 2013/021815 A1 | 2/2013 |
| WO | WO 2013/041878 A1 | 3/2013 |
| WO | WO 2013/057495 A2 | 4/2013 |
| WO | WO 2013/121193 A2 | 8/2013 |
| WO | WO 2013/121224 A1 | 8/2013 |
| WO | WO 2013/123379 A2 | 8/2013 |
| WO | WO 2013/153359 A1 | 10/2013 |
| WO | WO 2014/013260 A1 | 1/2014 |
| WO | WO 2014/019603 A1 | 2/2014 |
| WO | WO 2014/064443 A2 | 5/2014 |
| WO | WO 2014/064444 A1 | 5/2014 |
| WO | WO 2014/132343 A1 | 9/2014 |
| WO | WO 2014/158665 A1 | 10/2014 |
| WO | WO 2015/183871 A1 | 12/2015 |
| WO | WO 2015/193076 A1 | 12/2015 |
| WO | WO 2016/034591 A2 | 3/2016 |
| WO | WO 2016/059427 A1 | 4/2016 |
| WO | WO 2016/127007 A2 | 8/2016 |
| WO | WO 2016/172724 A1 | 10/2016 |
| WO | WO 2016/187519 A1 | 11/2016 |
| WO | WO 2017/061600 A1 | 4/2017 |
| WO | WO 2018/007819 A1 | 1/2018 |
| WO | WO 2019/063959 A1 | 4/2019 |
| WO | WO 2019/160925 A1 | 8/2019 |
| WO | WO 2020/183172 A1 | 9/2020 |

OTHER PUBLICATIONS

International Preliminary Report on Patentability for Application No. PCT/GB2021/051806, mailed Jan. 26, 2023.
[No Author Listed] Avanti Polar Lipids, Inc. Avanti Polar Lipids-Preparations of Liposomes. Www.avantilipids.com 5 pages. Jul. 1, 2014.
Aghdaei et al., Formation of artificial lipid bilayers using droplet dielectrophoresis. Lab Chip. Oct. 2008;8(10):1617-20. doi: 10.1039/b807374k. Epub Aug. 13, 2008.
Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.
Anrather et al., Supported membrane nanodevices. J Nanosci Nanotechnol. Jan.-Feb. 2004;4(1-2):1-22.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.
Bezrukov et al., Counting polymers moving through a single ion channel. Nature. Jul. 28, 1994;370(6487):279-81.
Bouaidat et al., Surface-directed capillary system; theory, experiments and applications. Lab Chip. Aug. 2005;5(8):827-36. Epub Jul. 1, 2005.

(56) References Cited

OTHER PUBLICATIONS

Bruggemann et al., Microchip technology for automated and parallel patch-clamp recording. Small. Jul. 2006;2(7):840-6.
Bull et al., Polymer Films on Electrodes. J. Electrochem Soc. May 1982;129(5):1009-1015.
Cheng et al., Discrete membrane arrays. J Biotechnol. Sep. 2000;74(3):159-74.
Cheng et al., Single Ion Channel Sensitivity in Suspended Bilayers on Micromachined Supports. Langmuir. 2001;17(4):1240-1242.
Danelon et al., Cell membranes suspended across nanoaperture arrays. Langmuir. Jan. 3, 2006;22(1):22-5.
Devereux et al., A comprehensive set of sequence analysis programs for the VAX. Nucleic Acids Res. Jan. 11, 1984;12(1 Pt 1):387-95.
Estes et al., Electroformation of giant liposomes from spin-coated films of lipids. Colloids Surf B Biointerfaces. May 10, 2005;42(2):115-23.
Fraikin et al., A high-throughput label-free nanoparticle analyser. Nat Nanotechnol. 2011;6(5):308-313. doi:10.1038/nnano.2011.24.
Funakoshi et al., Lipid bilayer formation by contacting monolayers in a microfluidic device for membrane protein analysis. Anal Chem. Dec. 15, 2006;78(24):8169-74.
Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.
Gonzalez-Perez et al., Biomimetic triblock copolymer membrane arrays: a stable template for functional membrane proteins. Langmuir. 2009;25(18):10447-10450. doi:10.1021/la902417m.
Hasanzadeh et al., Room-temperature ionic liquid-based electrochemical nanobiosensors. Trends Anal Chem. Dec. 2012;41:58-74.
Heron et al., Simultaneous measurement of ionic current and fluorescence from single protein pores. J Am Chem Soc. Feb. 11, 2009;131(5):1652-3. doi: 10.1021/ja808128s.
Hirano et al., Lipid Bilayers at Gel/Gel Interface for Ion Channel Recordings. Surf. Sci. Nanotech. 2008;6:130-133.
Holden et al., Functional bionetworks from nanoliter water droplets. J Am Chem Soc. Jul. 11, 2007;129(27):8650-5. Epub Jun. 16, 2007.
Horn, Avoiding Evaporation. Ibidi. Application Note 12. Mar. 29, 2012, pp. 1-3.
Hovis et al., Patterning and Composition Arrays of Supported Lipid Bilayers by Microcontact Printing. Langmuir. 2001;17:3400-3405.
Hromada et al., Single molecule measurements within individual membrane-bound ion channels using a polymer-based bilayer lipid membrane chip. Lab Chip. Apr. 2008;8(4):602-8. doi:10.1039/b716388f. Epub Feb. 29, 2008.
Ide et al., A novel method for artificial lipid-bilayer formation. Biosens Bioelectron. Oct. 15, 2005;21(4):672-7. Epub Jan. 26, 2005.
Ikariyama et al., Polypyrrole electrode as a detector for electroinactive anions by flow injection analysis. Anal. Chem. 1986, 58, 8, 1803-1806.
Ivanov et al., DNA tunneling detector embedded in a nanopore. Nano Lett. 2011;11(1):279-285. doi:10.1021/nl103873a.
Jeon et al., Long-term storable and shippable lipid bilayer membrane platform. Lab Chip. Oct. 2008;8(10):1742-4. doi: 10.1039/b807932c. Epub Aug. 22, 2008.
Jung et al., Detecting protein-ligand binding on supported bilayers by local pH modulation. J Am Chem Soc. Jan. 28, 2009;131(3):1006-14. doi: 10.1021/ja804542p. Author Manuscript, 23 pages.
Kam et al., Spatially Selective Manipulation of Supported Lipid Bilayers by Laminar Flow: Steps Toward Biomembrane Microfluidic. Langmuir. 2003;19(5):1624-1631.
Kasianowicz et al., Protonation dynamics of the alpha-toxin ion channel from spectral analysis of pH-dependent current fluctuations. Biophys J. Jul. 1995;69(1):94-105.
Khafizov, Single Molecule Force Spectroscopy Of Single Stranded Dna Binding Protein And Rep Helicase. University of Illinois at Urbana-Champaign Dissertation. 2012.
Kim et al., Liquid-slate field-effect transistors using electrowetting. Applied Physics Letters. 90:043507-1-043507-3.
Korolev et al., Major domain swiveling revealed by the crystal structures of complexes of E. coli Rep helicase bound to single-stranded DNA and ADP. Cell. Aug. 22, 1997;90(4):635-47.
Krantz Lab. Planar Lip Bilayer Electrophysiology Equipment. Department of Molecular & Cell Biology, University of California, Berkeley. Oct. 6, 2007. Last accessed at mcb.berkeley.edu/labs/krantz/equipment/blm.html on Nov. 26, 2014.
Kung et al., Printing via Photolithography on Micropartitioned Fluid Lipid Membranes. Adv. Materials. 2000;12(10):731-734.
Langecker et al., Synthetic lipid membrane channels formed by designed DNA nanostructures. Science. Nov. 16, 2012;338(6109):932-6. doi: 10.1126/science.1225624.
Le Pioufle et al., Lipid bilayer microarray for parallel recording of transmembrane ion currents. Anal Chem. Jan. 1, 2008;80(1):328-32. Epub Nov. 15, 2007.
Lee et al., Ion channel switch array: A biosensor for detecting multiple pathogens. Industrial Biotechnology. May 2005;1(1):26-31. doi:10.1089/ind.2005.1.26.
Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.
Lee et al., Polyelectrolyte Micropatterning Using Agarose Plane Stamp and a Substrate Having Microscale Features on Its Surface. Bull. Korean Chem. Soc., vol. 26(10):1539-1542 (2005).
Lewis et al., The Mesomorphic Phase Behavior of Lipid Bilayers. Structure Biological Membranes. 3rd Ed. Ed: Yeagle. CRC Press 2011. 19-89.
Li et al., Microfluidic system for planar patch clamp electrode arrays. Nano Lett. Apr. 2006;6(4):815-9.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Luan et al., Base-by-base ratcheting of single stranded DNA through a solid-state nanopore. Phys Rev Lett. Jun. 11, 2010;104(23):238103. Epub Jun. 10, 2010.
Mach et al., Miniaturized planar lipid bilayer: increased stability, low electric noise and fast fluid perfusion. Anal Bioanal Chem. Feb. 2008;390(3):841-6. Epub Oct. 31, 2007.
Majd et al., Hydrogel stamping of arrays of supported lipid bilayers with various lipid compositions for the screening of drug-membrane and protein-membrane interactions. Angew Chem Int Ed Engl. Oct. 21, 2005;44(41):6697-700.
Malmstadt et al., Automated formation of lipid-bilayer membranes in a microfluidic device. Nano Lett. Sep. 2006;6(9):1961-5.
Mangold et al., Reference electrodes based on conducting polymers. Fresenius J Anal Chem. Jun. 2000;367(4):340-2.
Mastrangeli et al., Challenges for Capillary Self-Assembly of Microsystems. IEEE Transactions. Jan. 2011;1(1):133-149.
Mastrangeli et al., Self-assembly from milli- to nanoscales: methods and applications. J Micro Microeng. 2009;19:083001.
Maurer et al., Reconstitution of ion channels in agarose-supported silicon orifices. Biosens Bioelectron. May 15, 2007;22(11):2577-84. Epub Nov. 13, 2006.
Mcalduff et al., Freestanding lipid bilayers as substrates for electron cryomicroscopy of integral membrane proteins. J Microsc. Feb. 2002;205(Pt 2):113-7.
Montal et al., Formation of bimolecular membranes from lipid monolayers and a study of their electrical properties. Proc Natl Acad Sci U S A. Dec. 1972;69(12):3561-6.
Moran-Mirabal et al., Micrometer-sized supported lipid bilayer arrays for bacterial toxin binding studies through total internal reflection fluorescence microscopy. Biophys J. Jul. 2005;89(1):296-305. Epub Apr. 15, 2005.
Ogier et al., Suspended Planar Phospholipid Bilayers on Micromachined Supports, Langmuir, vol. 16:5696-5701 (2000).
Onoe et al., Three-Dimensional Micro-Self-Assembly Using Hydrophobic Interaction Controlled by Self-Assembled Monolayers. J Micro Systems. Aug. 2004;13(4):603-611.
Parthasarathy et al., Protein patterns at lipid bilayer junctions. Proc Natl Acad Sci U S A. Aug. 31, 2004;101(35):12798-803. Epub Aug. 20, 2004.

(56) References Cited

OTHER PUBLICATIONS

Peterman et al., Ion Channels and Lipid Bilayer Membranes Under High Potentials Using Microfabricated Apertures. Biomedical Microdevices, vol. 4(3):231-236 (2002).

Polk et al., Ag/AgCl microelectrodes with improved stability for microfluidics, Sensors and Actuators B., vol. 114:239-247 (2006).

Rauf et al., Studies on sildenafil citrate (Viagra) interaction with DNA using electrochemical DNA biosensor. Biosens Bioelectron. May 15, 2007;22(11):2471-7. Epub Nov. 7, 2006.

Romer et al., Impedance analysis and single-channel recordings on nano-black lipid membranes based on porous alumina. Biophys J. Feb. 2004;86(2):955-65.

Sackmann, Supported membranes: scientific and practical applications. Science. Jan. 5, 1996;271(5245):43-8.

Sandison et al., Air-exposure technique for the formation of artificial lipid bilayers in microsystems. Langmuir. Jul. 17, 2007;23(15):8277-84. Epub Jun. 22, 2007.

Sandison et al., Rapid fabrication of polymer microfluidic systems for the production of artificial lipid bilayers. J. Micromech. Microeng., vol. 15:S139-S144 (2005).

Sapra et al., Lipid-coated hydrogel shapes as components of electrical circuits and mechanical devices. Sci Rep. 2012;2:848. doi: 10.1038/srep00848. Epub Nov. 14, 2012.

Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.

Schindler et al., Branched bimolecular lipid membranes. Biophys J. Sep. 1976;16(9):1109-13.

Schmidt et al., A Chip-Based Biosensor for the Functional Analysis of Single Ion Channels. Angew Chem Int Ed Engl. Sep. 1, 2000;39(17):3137-3140.

Shim et al., Stochastic sensing on a modular chip containing a single-ion channel. Anal Chem. Mar. 15, 2007;79(6):2207-13. Epub Feb. 9, 2007. Author Manuscript, 13 pages.

Smith et al., Micropatterned fluid lipid bilayer arrays created using a continuous flow microspotter. Anal Chem. Nov. 1, 2008;80(21):7980-7. doi: 10.1021/ac800860u. Epub Oct. 8, 2008. Author Manuscript, 17 pages.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Sun et al., Microfluidic static droplet arrays with tuneable gradients in material composition. Lab Chip. Dec. 7, 2011;11(23):3949-52. doi: 10.1039/c1lc20709a. Epub Oct. 12, 2011.

Suzuki et al., Highly reproducible method of planar lipid bilayer reconstitution in polymethyl methacrylate microfluidic chip. Langmuir. Feb. 14, 2006;22(4):1937-42.

Suzuki et al., Planar lipid bilayer reconstitution with a micro-fluidic system. Lab Chip. Oct. 2004;4(5):502-5. Epub Sep. 2, 2004.

Suzuki et al., Planar Lipid Membrane Array for Membrane Protein Chip. 17th IEEE International Conference on Micro Electro Mechanical Systems (MEMS), pp. 272-275 (2004).

Syms et al., Surface Tension-Powered Self-Assembly of Microstructures—The State of the Art. J Micro Systems. Aug. 2003;12(4):387-417.

Thorsen et al., Dynamic pattern formation in a vesicle-generating microfluidic device. Phys Rev Lett. Apr. 30, 2001;86(18):4163-6.

Urisu et al., Formation of high-resistance supported lipid bilayer on the surface of a silicon substrate with microelectrodes. Nanomedicine. Dec. 2005;1(4):317-22.

Vidinha et al., Ion jelly: a tailor-made conducting material for smart electrochemical devices. Chem Commun (Camb). Nov. 30, 2008;(44):5842-4. doi: 10.1039/b811647d. Epub Oct. 3, 2008.

Vulto et al., Microfluidic channel fabrication in dry film resist for production and prototyping of hybrid chips. Lab Chip. Feb. 2005;5(2):158-62. Epub Dec. 3, 2004.

Wagterveld et al., Ultralow hysteresis superhydrophobic surfaces by excimer laser modification of SU-8. Langmuir. Dec. 19, 2006;22(26):10904-8.

Watanabe et al., Electrical recording of Nanopore membrane proteins in a microfluidic device. The Papers of Technical Meeting on Bio Micro Systems, IEE Japa. 2010; BMS-10(7-27):5-8.

Yusko et al., Controlling protein translocation through nanopores with bio-inspired fluid walls. Nat Nanotechnol. Apr. 2011; 6(4): 253-260. Epub Feb. 20, 2011. doi: 10.1038/nnano.2011.12. Author Manuscript, 22 pages.

Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.

Zagnoni et al., Controlled delivery of proteins into bilayer lipid membranes on chip. Lab Chip. Sep. 2007;7(9):1176-83. Epub Jun. 27, 2007. Author Manuscript, 14 pages.

Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.

Third Party Observations for Application No. EP21749248.7, mailed Jul. 12, 2023.

Piper et al., Stable silicon-ionic liquid interface for next-generation lithium-ion batteries. Nat Commun. Feb. 25, 2015;6:6230. 10 pages. doi: 10.1038/ncomms7230.

Tomimatsu et al. Possible contamination of ionic liquids upon dissolution and absorption of rubber and resin components, Journal of Molecular Liquids. Mar. 15, 2019;278:78-85.

Fig. 8
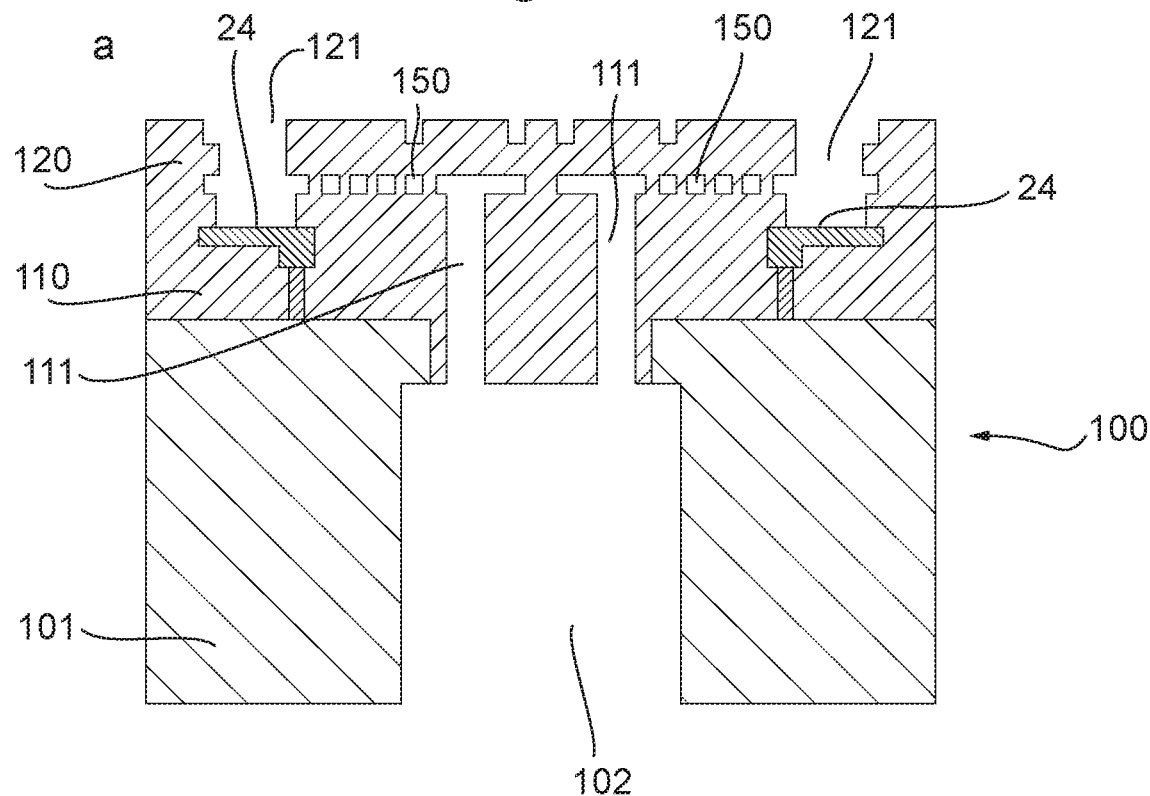
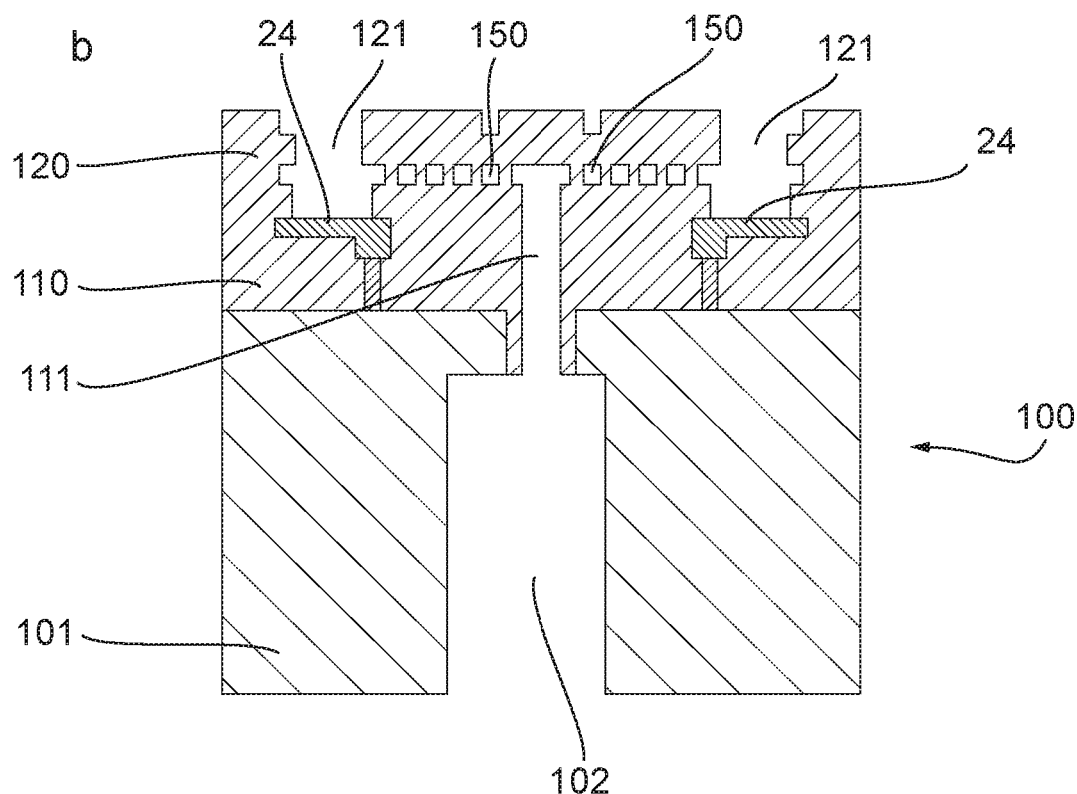

NANOPORE SENSING DEVICE

RELATED APPLICATIONS

This Application is a national stage filing under 35 U.S.C. 371 of International application number PCT/GB2021/051806, filed Jul. 14, 2021, which claims priority under 35 U.S.C. § 119(e) to U.S. Provisional application No. 63/053,122, filed Jul. 17, 2020, each of which is hereby incorporated herein by reference in its entirety.

TECHNICAL FIELD

The present invention relates to a nanopore sensing device.

BACKGROUND

Nanopore sensing devices have been developed for sensing a wide range of species, including single molecules such as polymer molecules. A known nanopore sensing device is a MinION™, manufactured and sold by Oxford Nanopore Technologies Ltd. The nanopore-based sensing therein employs the measurement of ionic current flow through a biological nanopore located in a highly resistive amphiphilic membrane. The MinION™ has an array of nanopore sensors. As a molecule, such as a polymer analyte e.g. DNA, is caused to translocate a nanopore, measurement of the fluctuations in ionic current may be used to determine the sequence of the DNA strand. Nanopore devices for detection of analytes other than polynucleotides such as proteins are also known from WO2013/123379.

Many nanopore sensing devices, such as MinION™, use biological nanopores, but an alternative is to use solid state nanopores. An example of a nanopore sensing device using solid state nanopores is disclosed in WO2016/127007, hereby incorporated by reference in its entirety. The performance of solid-state nanopore sensors is limited by the sensing components, manufacturing techniques and their tolerances, which can occur as a result of variation in the formation of the nanopore or the assembly of the sensor. These and other factors detriment the bandwidth, sensitivity and ability to control such nanopore sensors.

SUMMARY

The present invention is concerned with the overcoming problems associated with implementing a nanopore sensor device having a plurality of nanopore sensors.

According to an aspect of the invention, there is provided a nanopore sensing device comprising: first and second chambers; a planar structure provided with plural fluidic passages extending between the first and second chambers, the planar structure being configured to support nanopores in membranes across respective passages; sensor electrodes arranged to sense a fluidic electrical potential in respective passages between the nanopores and the second chamber, wherein the passages comprise planar fluidic resistor portions between the sensor electrode and the second chamber, the planar fluidic resistor portions extending in a planar direction of the planar structure and being configured to form a fluidic resistor.

By providing the planar fluidic resistor portion a voltage divider is formed across the sensor electrode including the resistance of the nanopore in one leg and including the resistance of the planar fluidic resistor portion in the other leg. As a result, the fluidic electrical potentials sensed in the passages by the sensor electrodes allow sensing of the current flowing through the passage and hence the nanopores. This allows for nanopore sensing.

Furthermore, the formation of the planar fluidic resistor portion extending in a planar direction of the planar structure improves the ease of manufacture compared to a fluidic resistor portion formed by an access hole extending through the thickness of the planar structure. This is because typical resistances of nanopores mean that the fluidic resistor portion needs to be provided with a relatively high resistance to perform the voltage divider with the nanopore. Thus, fluidic resistor portions formed by access holes extending through the thickness of the planar structure need to be relatively long and to have a relatively high aspect ratio which is difficult to manufacture. In contrast, a planar fluidic resistor portion extending in a planar direction of the planar structure is in principle more easy to form. However, their configuration and formation remains a technical issue, and some of the following aspects of the present invention are concerned with improving the ease of manufacture.

The fluidic resistor portion can be linear in shape. The fluidic resistor portion can have a continuous linear shape, with no bends or turns. The fluidic resistor portion can be linear in shape and extend in a direction normal to the planar structure. The fluidic resistance of the fluidic resistor portion can be less than the resistance of the nanopore. The fluidic resistance of the fluidic resistor portion can be between less than 50% and about 1% of the resistance of the nanopore. The fluidic resistance of the fluidic resistor portion can be about 10% of the resistance of the nanopore. In one aspect, the planar structure comprises: a nanopore support layer that is configured to support the nanopores in the membranes extending across the passages; and a further layer in which the planar fluidic resistor portions are formed.

By forming the planar fluidic resistor portions in a different layer from the nanopore support layer supports the nanopores in the membranes, the nanopore support layer may be designed and manufactured with suitable properties for the nanopore support, while allowing the planar the planar fluidic resistor portions to be formed in a further layer having different material properties.

In some types of embodiment, the nanopore support layer is provided with wells opening into the first chamber, the wells forming part of the passages and being configured to support said nanopores in said membranes extending across the wells.

The further layer may be a dielectric layer. This facilitates manufacture of the planar fluidic resistor portions by permitting use various techniques suitable for processing dielectric materials, for example deposition and removal process.

The first and second chambers may be on opposite sides of the planar structure so that the passages extend through the planar structure. In that case, the substrate may be provided with access holes which extend therethrough and form part of the passages.

In another aspect which may be combined with a separate nanopore support layer but is not dependent thereon, the first and second chambers are on opposite sides of the planar structure so that the passages extending through the planar structure. In that case, the planar structure may comprise a substrate; and a further layer that is supported by the substrate, with the planar fluidic resistor portions being formed in the further layer, and the substrate being provided with accessholes extending therethrough to form part of the passages.

This facilitates manufacture of the planar fluidic resistor portions by allowing the further layer to be processed on the substrate. For example, the further layer may be a dielectric layer which, as mentioned above, facilitates manufacture of the planar fluidic resistor portions by permitting use of various techniques suitable for processing dielectric materials, for example deposition and removal process.

In some embodiments, the further layer is between the first chamber and the substrate. Advantageously, this locates the further layer in which the planar fluidic resistor portions are formed closer to the nanopore within the passages.

Advantageously, each access hole may be shared by plural passages by being fluidically connected in common to plural planar fluidic resistor portions. This permits the area density of the passages and nanopores across the area of the planar structure to be increased.

The substrate may be a semiconductor wafer. This permits the planar fluidic resistor portions to be formed in the further layer using conventional semiconductor processing techniques.

In addition, the planar structure may further comprise a circuit layer supported by the semiconductor wafer, the circuit layer comprising circuit components connected to the sensor electrode. This allows the semiconductor wafer both to provide a substrate supporting both the circuit layer and the further layer in which the planar fluidic resistor portions are formed.

In this case, advantageously, the circuit layer is formed on the semiconductor wafer and the dielectric layer is formed on the circuit layer. This order simplifies the manufacture to provide the circuit layer and the further layer in which the planar fluidic resistor portions are formed.

In other embodiments, the planar structure further comprises a semiconductor wafer having a circuit layer supported thereby, the circuit layer comprising circuit components connected to the sensor electrode, the semiconductor wafer and the circuit layer is provided with access holes which extend therethrough and form part of the passages, and the substrate is bonded to the semiconductor wafer between the semiconductor wafer and the second chamber.

In other embodiments, the planar structure comprises: a substrate; a circuit layer supported by the semiconductor wafer, the circuit layer comprising circuit components connected to the sensor electrode; and a nanopore support layer that is configured to support the nanopores in the membranes extending across the passages, the planar fluidic resistor portions being formed in the nanopore support layer. This facilitates manufacture of the planar fluidic resistor portions by permitting various techniques suitable for processing the nanopore support layer.

In this case, the nanopore support layer may be provided with wells opening into the first chamber, the wells forming part of the passages and being configured to support said nanopores in said membranes extending across the wells.

The first and second chambers may be on opposite sides of the planar structure, in which case the passages extend through the planar structure. The substrate can be provided with access holes, forming part of the passages, which extend therethrough.

An access hole may be shared by plural passages by being fluidically connected in common to plural planar fluidic resistor portions. When an access hole is shared between two or more passages the resistance of the access hole is configured to inhibit crosstalk between passages. The resistance of a common access hole can be negligible within the passage.

The substrate may be a semiconductor wafer.

In any of the embodiments, advantageously, the planar fluidic resistor portion may extend along a tortuous path. This facilitates packaging of a planar fluidic resistor portion with sufficient length to provide a desired resistance within a discrete area on the planar structure, thereby assisting with increasing the area density of the nanopore sensors.

In any of the embodiments, advantageously, the planar fluidic resistor portion may comprise sections each extending in the planar direction of the planar structure but at different depths within the planar structure. This facilitates packaging of a planar fluidic portion with sufficient length to provide a desired resistance within a discrete area on the planar structure, thereby assisting with increasing the area density of the nanopore sensors. The sections at different depths may overlap.

BRIEF DESCRIPTION OF THE DRAWINGS

To allow better understanding, embodiments of the present invention will now be described by way of non-limitative example with reference to the accompanying drawings, in which:

FIGS. 8a and 8b are cross-sectional views of the planar structure with second and third modified constructions;

DETAILED DESCRIPTION OF THE INVENTION

Figure 1:
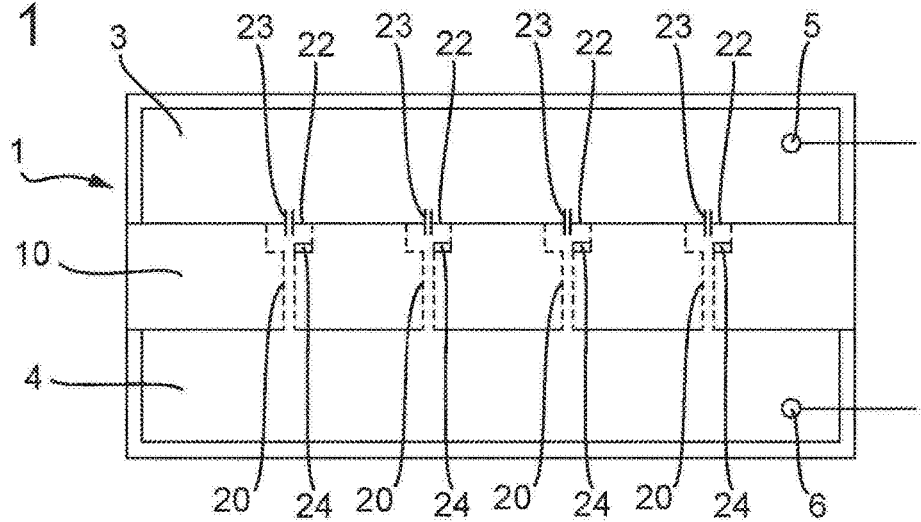
FIG. 1 is a cross-sectional view of a nanopore sensing device.

FIG. 1 shows a nanopore sensing device 1 that is arranged as follows.

The nanopore sensing device 1 comprises a first chamber 3 and a second chamber 4 with a planar structure 10 between the first and second chambers 3, 4. The first and second chambers 3, 4 are filled with fluid, such as an ionic solution or ionic liquid, in use. The first and second chambers 3, 4 are shown schematically in FIG. 1 but may be arranged with any suitable structure.

The first and second chambers 3, 4 may be closed or may arranged as part of flow cells permitting flow of solution therethough.

The planar structure 10 is provided with plural fluidic passages 20 that extend between the first and second chambers 3, 4. Thus, the fluidic passages 20 are filled with fluid, in use, and is fluidically connect the first and second chambers 3, 4. Each of the fluidic passages 20 is connected to the first and second chambers 3, 4, so the nanopores 22 lies in parallel paths of fluidic communication. The plural fluidic passages 20 may be arranged in an array in two dimensions across the planar structure 10.

In FIG. 1, the construction of the planar structure 10 is not shown FIG. 1 and so the fluidic passages 20 are shown schematically. The configuration of the planar structure 10 and the fluidic passages 20 is described in detail below.

In this example, as the first and second chambers 3, 4 are on opposite sides of the planar structure 10, the passages 20 extend through the planar structure 10. However, as an alternative, the first and second chambers 3, 4 could be arranged in different locations on the same side of the planar structure 10.

In this example, drive electrodes 5, 6 are provided in the first and second chambers 3, 4. In use, an electrical potential difference may be applied across the drive electrodes 5, 6 and therefore across each fluidic passage 20 to induce an analyte to flow between the first and second chambers 3, 4. The drive electrodes 5, 6 may be configured to apply substantially the same potential difference across all the fluidic passages 20. Additionally, or alternatively, the nanopore sensing device 1 can be configured to induce an analyte flow through the fluidic passages 20 using other techniques.

The first chamber 3 may function as a cis chamber and hold an analyte to be analysed by the nanopore sensing device 1. The second chamber 4 may function as a trans chamber and receive the analyte from the first chamber 3.

As described in more detail below, the planar structure 10 supports nanopores 23 in membranes 22 that extend across respective passages 20. Examples of suitable membranes 22 and nanopores 23 are described below.

The fluidic passages 20 are each provided with a sensor electrode 24 arranged to sense a fluidic electrical potential in the respective passage 20 between the nanopores 23 and the second chamber 4. As an analyte passes through a nanopore 22, the fluctuation in electrical potential caused by changes in ion current flow is detected by the sensor electrode 24. Thus, the passage 20 and the sensor electrode 24 formed therein act as respective sensors in the nanopore sensor device 1.

Figure 2:
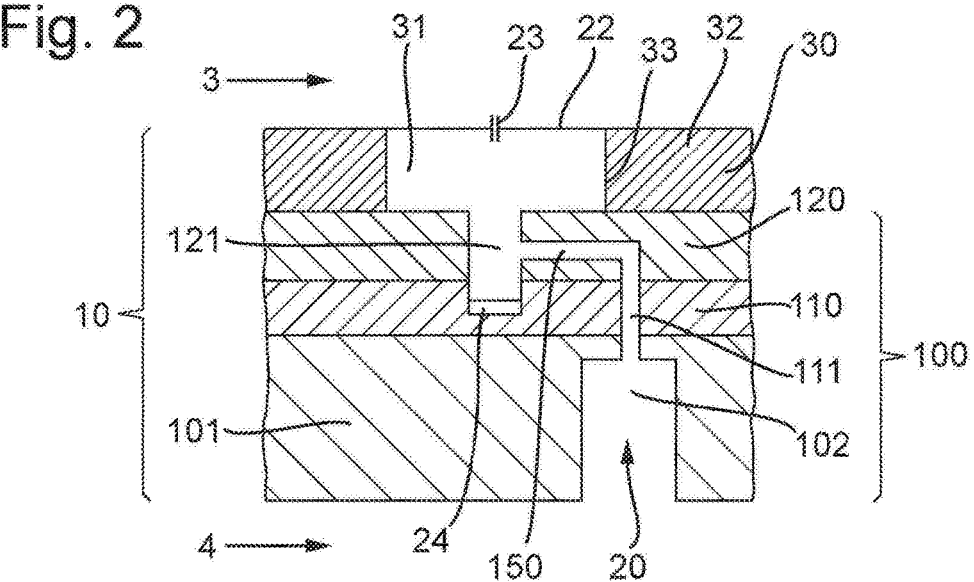
FIG. 2 is a cross-sectional view of a planar structure of the nanopore sensing device.

FIG. 2 illustrates the construction of the planar structure 10, showing a single one of the plural fluidic passages 20 for clarity, as follows.

The planar structure 10 comprises a nanopore support layer 30 and a base layer 100 which are fixed together.

The nanopore support layer 30 is configured to support the nanopores 23 in the membranes 22 extending across the passages 20. In particular, the nanopore support layer 30 is provided with wells 31 opening into the first chamber 3. The wells 31 form part of the passages 20. The wells 31 are configured to support the membranes 22 extending across the passages 20, specifically extending across the openings of the wells 31, and thereby to support the nanopores 22. The nanopore support layer 30 includes a wall layer 32 comprising walls 33 that define the wells 31.

The nanopore support layer 30 may be made of any suitable material, for example: ceramics such as silicon dioxide or silicon nitride; photo resist such as SU-8 or TMMF/TMMR; plastic such as acrylic (PMMA); or epoxy resin.

Figure 3:
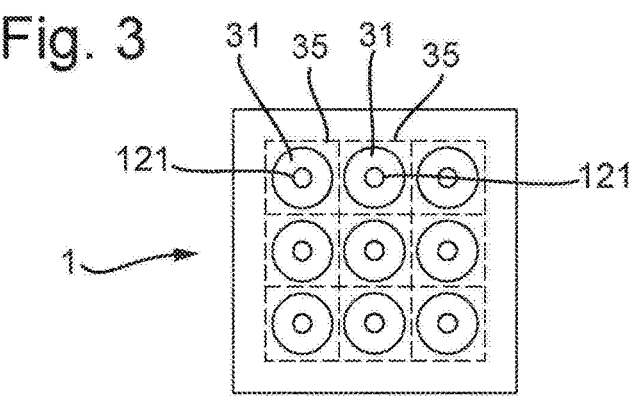
FIG. 3 is a plan view of the planar structure.

FIG. 3 shows an example in which the plural wells 31 are arranged in a plane in a regular planar array having a repeating structure in plan view (from above in FIG. 2). FIG. 3 shows only nine wells 4 for simplicity, but in general the nanopore support layer 30 may have any number of wells 31, typically being much larger than nine, for example of the order of 1000 or more, practically in the order of 100,000, and feasibly up to 5,000,000 or more. Each of the wells 31 and the corresponding passages 20 is arranged within a respective footprint 35.

The base layer 100 is between the nanopore support layer 30 and the second chamber 4 and includes the following layers. The base layer 100 includes a semiconductor wafer 101 which forms a substrate in this example and supports a circuit layer 110 and a dielectric layer 120. The circuit layer 110 comprises circuit components connected to the sensor electrodes 24. The circuit components in respect of each passage 20 are arranged within the same footprint 35 as the passage 20.

The semiconductor wafer 101 is typically made of silicon, but can in principle be any semiconductor material which is suitable as a support for a circuit layer 110, such as silicon dioxide, quartz, glass, amorphous aluminium oxide or sapphire.

The dielectric layer 120 provides a planar fluidic resistor portion 150 that forms part of the passage 20, so forms the further layer in this example. In this manner, the fluidic passage 20 provides a fluidic resistor between the sensor electrode 24 and the second chamber 4. More specifically, the fluidic passage 20 through the base layer 100 includes the following portions that are fluidically connected in series:

the well 31, or access thereto, as described above;
a dielectric access hole 121 that extends from the well 31 through the dielectric layer;
the planar fluidic resistor portion 150 formed in the dielectric layer and fluidically connected to the dielectric access hole 121;
a circuit layer access hole 111 extending through the circuit layer 110 and fluidically connected to the planar fluidic resistor portion 150; and
a wafer access hole 102 extending through the semiconductor wafer 101 and fluidically connected to the circuit layer access hole 111.

The sensor electrode 24 is formed in the dielectric access hole 121.

Figure 4:
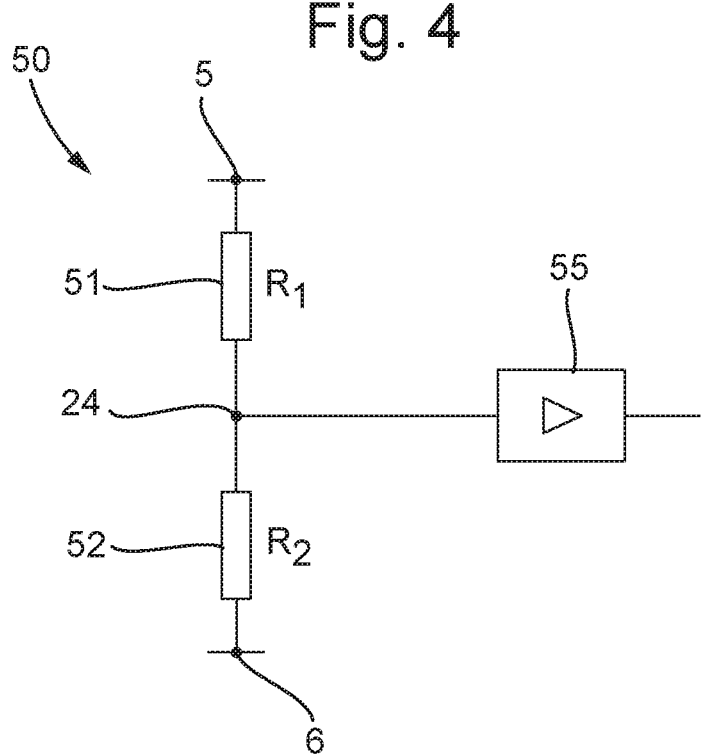
FIG. 4 is a diagram of a circuit of the nanopore sensing device.

The planar fluidic resistor portion 150 is configured to form a fluidic resistor. In this manner, the fluidic passages 20 are configured to provide fluidic resistors between the sensor electrode 24 and the second chamber 4 as will now be described with reference to FIG. 4 which is a diagram of a circuit of the nanopore sensing device 1.

As a result, the passage 20 forms a voltage divider 50 with the nanopore 23 such that the sensor electrode 24 is positioned between two legs 51 and 52 of the voltage divider 50. The first leg 51 of the voltage divider 50 is formed between the first drive electrode 5 and the sensor electrode 24, and the second leg 52 of the voltage divider 50 is formed between the sensor electrode 24 and the second drive electrode 6.

The resistance of the nanopore 23 with any additional solution resistance between first drive electrode 5 and the sensor electrode 24 is present in a first leg 51 of the voltage divider 50. The well 31 and dielectric access hole 121 may be designed to have a minimal fluidic resistance compared to the nanopore 23.

The fluidic resistance of the planar fluidic resistor portion 150 is present in the second leg 52 of the voltage divider 50. The circuit layer access hole 111 and the wafer access hole 102 may be designed to provide a fluidic resistance that is negligible compared to the fluidic resistance of the planar fluidic resistor portion 150, but this is not essential and they may be designed to provide additional fluidic resistance.

The first and second chambers 51, 52 also have a negligible fluidic resistance compared to the passage 20 due to the relatively narrow cross-sectional area of the passage 20.

A sensor circuit 55 is configured to sense the electrical potential of the fluid at the sensor electrode 24 in the passage 20. As a result of the voltage divider 50, the fluidic electrical potentials sensed in the passage 20 by the sensor electrode 24 permits sensing of the current flowing through the passage 20 and hence the through the nanopore 23. The sensor electrode 24 can detect fluctuations in voltage as matter, such as a molecule on a strand of DNA, translocates through the nanopore 23. This provides nanopore sensing.

The sensor electrode 24 lies between the nanopore 23 and the planar fluidic resistor portion 150. Although the configuration in FIG. 2 is an example, the sensor electrode 24 can be located elsewhere in the passage 20, for example in the well 31.

In some embodiments, the sensor electrode 126 can function as a terminal (e.g. base or gate) of a transistor device for measuring electrical potential of the fluid at the location of the sensor electrode 24.

Some or all of the components of the sensor circuit 55 are formed in the circuit layer. 110. Such components may include, for example, any one or more of: a transistor device of which the sensor electrode 24 functions as a terminal (e.g. base or gate), amplifiers, gate circuits and so on. Where only some of the components of the sensor circuit 55 are formed in the circuit layer 110, the remainder of the sensor circuit 55 may be formed in a separate integrated circuit chip connected to the circuit layer 150.

Considerations in the design of the planar fluidic resistor portion 150 and the overall passage 20 are as follows.

The passage, and in particular the planar fluidic resistor portion 150, can be configured such that the resistance of the first and second legs 51, 52 of the voltage divider 50 are substantially matched when the passage 22 is filled by fluid, and relatively high relative to the resistance of fluid in the first and second chambers 3, 4 such that the resistance of the first and second chambers 3, 4 does not appreciably influence the measurements.

The signal-to-noise ratio may be optimised by selecting the fluidic resistances of the first and second legs 51, 52 of the voltage divider 50 to be equal. However, this is not essential and the fluidic resistance of the planar fluidic resistor portion 150 may be varied to take account of other factors, while still obtaining an acceptable signal-to-noise ratio. An acceptable signal-to-noise ratio may be achieved with the fluidic resistance of the second leg 52 of the voltage divider 50 being significantly less than the resistance of first leg of the voltage divider, for example with the fluidic resistance of the second leg 52 of the voltage divider 50 being 10% or less of the resistance of first leg 51 of the voltage divider 50, for example 2% thereof. In some embodiments, a lower limit on the fluidic resistance of the second leg 52 of the voltage divider 50 may be set by the desired signal to noise ratio.

Other factors that may be considered in the selection of the fluidic resistance of the second leg 52 of the voltage divider 50, and specifically the planar fluidic resistor portion 150, are as follows.

As the fluidic resistance of the second leg 52 increases, the diffusion of ions decreases, causing an increased depletion of ions near the pore, and thereby causing a decay of the signal over the timescale of a typical event over which a signal is obtained. In order to increase the limit on read length caused by this effect, the fluidic resistance of the planar fluidic resistor portion 150 may be reduced. In many embodiments, this factor may place an upper limit on the fluidic resistance of the planar fluidic resistor portion 150. As the fluidic resistance of the planar fluidic resistor portion 150 increases, the variation in the voltage across the nanopore 23 increases, which can complicate signal processing. In order to limit this effect, the fluidic resistance of the planar fluidic resistor portion 150 may be reduced. Reducing the fluidic resistance of the planar fluidic resistor portion 150 may increase bandwidth or provide leeway for additional capacitance in the passage 20 or the membrane 22.

Taking into account these factors, the fluidic resistance of the second leg of the voltage divider may be less than the resistance of the nanopore 23, typically at most 50%, or at most 25% of the resistance of the nanopore 23. In some embodiments, the optimal fluidic resistance of the second leg 52 of the voltage divider 50 may be around 10% of the resistance of the nanopore 23.

When reducing the ratio of the fluidic resistance of the second leg 52 of the voltage divider 50 to the resistance of the first leg 51 of the voltage divider 50, the signal to noise ratio does not scale linearly with that resistance ratio. For example, in some embodiments when the fluidic resistance of the second leg 52 of the voltage divider 50 is around 10% of the resistance of the nanopore 23, then the signal to noise ratio is around 30% of its optimal value.

Figure 5:
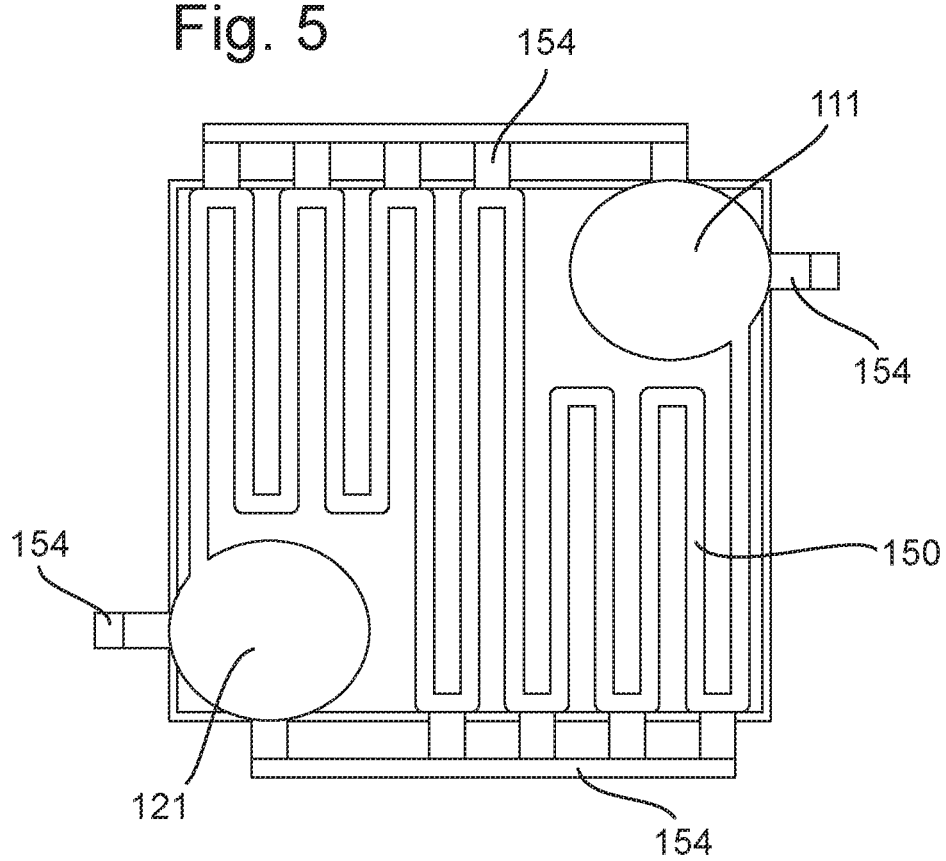
FIG. 5 is a plan view of a planar fluidic resistor portion that can be formed in a dielectric layer of the planar structure.

FIG. 5 illustrates an example of the planar fluidic resistor portion 150 which is arranged as follows.

The planar fluidic resistor portion 150 extends in a planar direction of the planar structure 10 along a tortuous path between the dielectric access hole 121 and the circuit layer access hole 111. By providing the planar fluidic resistor portion 150 with such a planar configuration it is can be manufactured in the dielectric layer 120. By providing the planar fluidic resistor portion 150 with a tortuous path, the planar fluidic resistor portion 150 may be provided with sufficient length while being packaged within a discrete area on the planar structure 10, that being an approximately square area in this example within the footprint 35.

In this example, the tortuous path of the fluidic resistor portion 150 is rectilinear and comprises plural straight legs extending back and forth. More generally, the planar fluidic resistor portion 150 could be provided with any suitable tortuous path, being any path that is nota straight line between its ends, ranging including paths that are much simpler or much more complex to that shown in FIG. 5. For example, a simple variation is for the tortuous path could comprise plural legs extending back and forth in a similar manner, but being a curved configuration, rather than being rectilinear. In other examples, the tortuous path could have some other curved shape, including a spiral shape.

The geometry of the planar fluidic resistor portion 150, in particular its path length and cross-sectional area are designed to provide the desired fluidic resistance, in conjunction with the fluid with which it is to be filled. That is, the fluidic resistance of the planar fluidic resistor portion 150 can be varied by varying its length, cross-sectional area and the ionic concentrations of the fluids therein. For example, to increase the fluidic resistance, the planar fluidic resistor portion 150 can be configured with an increased ratio of length to cross-sectional area and/or a lower ionic concentration. The passage may be provided with a lower ionic concentration than the first and/or second chambers 3, 4, because maintenance of a relatively high ionic concentration in the first and second chambers 3, 4 improves the signal to noise ratio.

In embodiments, the planar fluidic resistor portion 150 may have a length of at least 1 μm, at least 10 μm, at least 100 μm, or at least 1000 μm.

In embodiments, the planar fluidic resistor portion 150 may have cross-section having a characteristic dimension (for example the square root of the area) that is at most 100 μm, at most 10 μm, at most 1 μm, or at most 10 nm.

In general, any length and cross-section may be chosen together.

In very general terms, the passage 20 could have any geometry that provides ameasurable signal at the sensor electrode 24. The measurable signal will depend on the measurement circuit, bandwidth, noise etc, but may typically be at least 1 μV, at least 10 μV, at least 100 μV, or at least 1 mV.

Some methods for forming the planar structure 10 are as follows.

In some of these methods, the planar fluidic resistor portions 150 are formed in the dielectric layer 120. This permits use of various techniques suitable for processing dielectric materials, for example deposition and removal processes, thereby facilitating manufacture of the planar fluidic resistor portions 150.

Also, in some of these methods, the circuit layer 110 is formed on the semiconductor wafer 101 and the dielectric layer 120 is formed on the circuit layer 110, and is therefore between the first chamber 3 and the semiconductor wafer 101. This again simplifies the manufacture because the circuit layer 110 may be formed using conventional semiconductor processing techniques and then the planar fluidic resistor portions 150 is formed in the dielectric layer 120 on top. This facilitates the construction of the entire base layer 100 using similar techniques, typically as part of a common process in a semiconductor fabrication facility. It also avoids the need for a separate bonding process as would be needed the planar fluidic resistor portions 150 are formed on a substrate separate from the semiconductor wafer 101 on which the circuit layer 110 is formed.

FIGS. 6a-6j show a series of views of layers being processed during a method of manufacture which is performed as follows. The base layer 100 is fabricated from a semiconductor wafer 101, for example a single complementary metal-oxide semiconductor (CMOS) silicon wafer. FIG. 6a shows the semiconductor wafer 101 prior to the fabrication of the structure of the base layer, with deep trench isolation (DTI) and a connection in the circuit layer 110 for the sensor electrode 24.

In FIG. 6b, the metal sensor electrode 24 has been deposited. In this example, the sensor electrode 24 is a platinum electrode approximately 100 nm thick, which is deposited by sputtering, evaporation, or plating as Pt is not a standard metal in a typical CMOS foundry. Passivation of the surface and open electrode has been performed. The passivation can be plasma-enhanced chemical vapor deposition (PECVD) low stress nitride or oxynitride. A thickness of 500 nm-1 μm is sufficient for passivation, since further passivation layers will deposited later in the process. A circuit layer access hole 111 is formed through the circuit layer 110, specifically through the region of the DTI, although generally the circuit layer access hole 111 may be formed in other regions of the circuit layer 110. Typically, the circuit layer access hole 111 through the DTI is approximately 6 μm in diameter and 20 μm deep.

Figure 6:
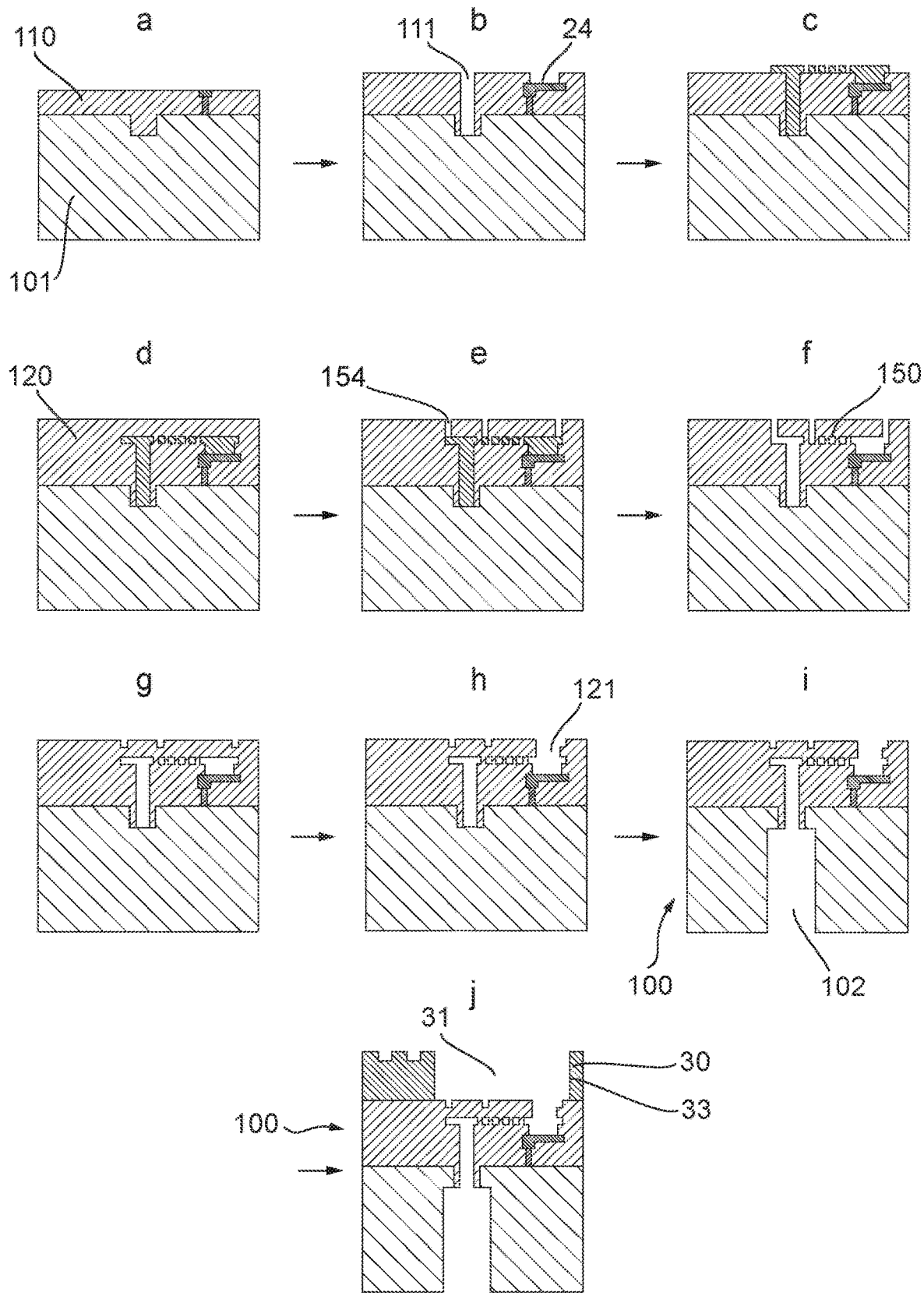
FIGS. 6a-6j are a series of cross-sectional views of layers being processed during manufacture of the planar structure.

FIG. 6c shows that a sacrificial polymer coating has been deposited via a lithography process. The sacrificial polymer can be polyimide or any other compatible polymer. The sacrificial polymer coating is formed in the shape of the channels of the planar fluidic resistor 15 portion 150 and also fills the circuit layer access hole 111. The thickness of the sacrificial polymer defines the thickness of the planar fluidic resistor portion 150, which in this example is approximately 300 nm. The width in the plane of the channels making up the tortuous path of the planar fluidic resistor portion 150 will be chosen by the micro-electromechanical system (MEMS) foundry. In this example, the width is approximately 1 μm. For larger structures, for example where the width in the plane of the channels is larger, supporting pillars along the tortuous path might be necessary. These can be formed by creating additional holes in the sacrificial polymer layer (not shown in FIG. 6).

In FIG. 6d, a thin passivation layer is deposited that forms the lower portion of the dielectric layer 120. The thin passivation layer can be the same PECVD low stress nitride or oxynitride as used previously in the process. The thin passivation layer needs to be of a minimum thickness to hold structural integrity during later stages of the manufacturing process, but also need to be thin enough to permit the fabrication and later filling in of vias. For the above example of a 1 μm width in the plane of the channels, a thickness of 1-2 μm for the thin passivation layer is appropriate.

In the step shown in FIG. 6e, open vias 154 are formed through the thin passivation layer to provide access to the sacrificial polymer (as shown in FIG. 5). The vias 154 expose the sides of the sacrificial polymer for the etching, dissolving or plasma ashing process to remove the sacrificial polymer. For a high aspect ratio channel such as used in the tortuous path of the planar fluidic resistor portion 150, multiple locations along the tortuous path need to be exposed to reduce the etch aspect ratio. This can be promoted by the design of the tortuous path of the planar fluidic resistor portion 150. FIG. 6f shows the state following plasma ashing or etching of the sacrificial polymer.

In FIG. 6g, a thick passivation layer is deposited to fill in the vias 154 that were used to provide access to the sacrificial polymer. The thick passivation layer (also referred to as a fill-in layer) should be much thicker than the earlier thin passivation layer, but can be formed from the same PECVD low stress nitride or oxynitride material. In this example, a thickness of approximately 5 μm is used. This allows the thick passivation layer to hold the structure integrity of the planar fluidic resistor portion 150. Following this, in FIG. 6h, the thick passivation layer is opened above the sensor electrode 24 to form the dielectric access hole 121.

In FIG. 6i, the semiconductor wafer 101 is ground down from below to thin it. In this example, the semiconductor wafer 101 is thinned to approximately 200-400 μm. Additionally, or alternatively, the semiconductor wafer 101 can be ground down at the beginning or middle of the process. This reduces the aspect ratio for the deep reactive ion etching (DRIE) process used to form the wafer access hole 102. During the thinning process, the front side of the semiconductor wafer, which now holds the structures deposited in earlier steps, is protected. The wafer access hole 102 is formed by DRIE, which is stopped at the DTI that holds the circuit layer access hole 111. Since the wafer access hole 102 is not part of the planar fluidic resistor portion 150, its diameter can be larger than the width of the tortuous path, e.g. approximately 20 μm, and without thick dielectric. This is a relatively easy process for a 40-50 μm pitch chip.

Following this step, the complete base layer 100 is formed. Following this, the rear (lower) side of the semiconductor wafer 101 is supported, and the protection/support removed from the front/upper side. The nanopore support layer 30 is then formed by further lamination and lithography on the front/upper side of the base layer 100 to create the completed planar structure 10, shown in FIG. 6j. Final dicing can then be performed to divide the semiconductor wafer 101 as appropriate.

This invention has the advantage that the base layer 100 can be manufactured using a single conventional semiconductor wafer (such as bulk CMOS). This includes fabrication of the planar fluidic resistor portion 150 with sacrificial polymer channels deposited directly on top of the semiconductor wafer. The method further uses DTI to separate the circuit layer 110 from the wafer access hole 102, and the wafer access holes 102 do not provide significant fluidic resistance, such that the planar fluidic resistor portion 150 can be the main determiner of the fluidic resistance in the second leg 52 of the voltage divider.

The nanopore sensing device 1 shown in FIG. 2 and described above is merely an example, and various alternatives are possible. Some non-limitative examples of such alternatives will now be described.

As in the example shown in FIGS. 6a-6j, the planar fluidic resistor portion 150 is formed in the dielectric layer 120 at the interface with the circuit layer 110, for example as shown in FIG. 6c. Alternatively, the planar fluidic resistor portion 150 may be formed at any other depth in the dielectric layer 120. As a first example of such an alternative, the planar fluidic resistor portion 150 may be formed in the dielectric layer 120 at a position separated from the interface with the circuit layer 110 and separated from the outer surface of the dielectric layer 120 which forms an interface with the nanopore support layer 30. FIG. 2 schematically illustrates this example. As a second example of such an alternative, the planar fluidic resistor portion 150 maybe formed in the dielectric layer 120 at the outer surface of the dielectric layer 120 which forms an interface with the nanopore support layer 30.

In the examples shown in FIG. 2 and FIGS. 6a-6j, the circuit layer 110 is formed on the semiconductor wafer 101 and the dielectric layer 120 is formed on the circuit layer 110, which provides the advantages described above. However, as an alternative, the dielectric layer 120 may be disposed between the circuit layer 110 and the semiconductor wafer 101. This alternative may be manufactured using similar techniques to those described above with respect to FIG. 6aj, except that the dielectric layer 120 is formed on the semiconductor wafer 101 before the circuit layer 110.

Figure 7:
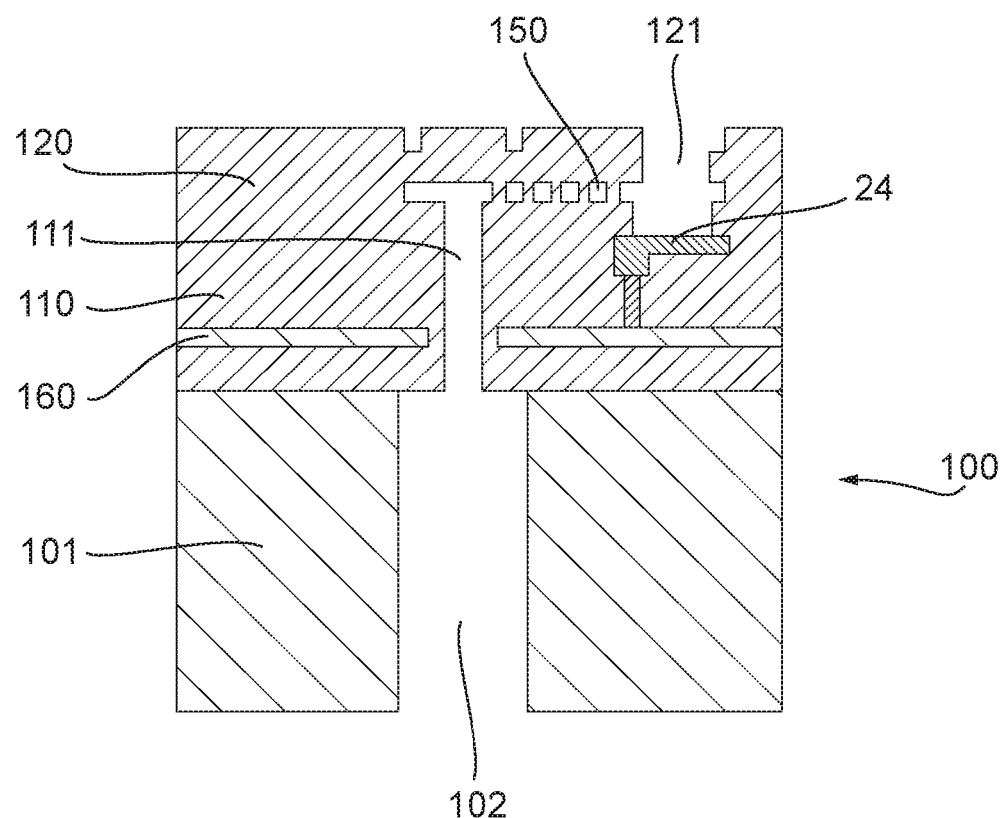
FIG. 7 is a cross-sectional view of the planar structure with a first modified construction.

A silicon-on-insulator (SOI) CMOS wafer can be used in this manufacturing method with very minimal modification to the methods described above. By way of example, FIG. 7 shows a base layer 100 manufactured using an SOI semiconductor wafer 101, which includes an insulator layer 160 (often a buried oxide) that can help to reduce parasitic resistance in the semiconductor wafer. The only requirement of the SOI wafer is that the insulator layer 160 should be thick enough to provide a reliable DRIE etch stop. A suitable example is a 1 μm buried oxide (BOX) layer. Such materials are commonly available in semiconductor manufacturing, and so these improvements can be applied directly to existing SOI CMOS wafers using existing equipment already used for prior art devices, so that the new designs can easily be implemented.

Considerations about the area density of the respective sensors formed by the passages 20 and associated in the nanopore sensor device 30 will now be described.

In some embodiments, the area density of the sensors may be relatively low, for example of 100 per mm$^2$ (corresponding to a square footprint 35 of side 100 μm). In such a case, the circuit layer access hole 111 and the wafer access hole 102 may be designed to provide a fluidic resistance that is negligible compared to the fluidic resistance of the planar fluidic resistor portion 150.

However a range of densities are possible. By way of example, in one embodiment, the area density of the sensors may be 400 per mm$^2$ (corresponding to a square footprint 35 of side 50 μm), in which case the length of the planar fluidic resistor portion 150 may be 250 μm and the cross-sectional area of the planar fluidic resistor portion 150 may be 0.3 μm$^2$ (e.g. 0.3 μm by 1 μm). In another embodiment, the area density of the sensors may be 2500 per mm$^2$ (corresponding to a square footprint 35 of side 20 μm), in which case the length of the planar fluidic resistor portion 150 may be 75 μm and the cross-sectional area of the planar fluidic resistor portion 150 may be 0.09 μm$^2$ (e.g. 0.3 μm by 0.3 μm).

As the area density of the sensors increases and the area of the footprint 35 decreases, it may be become difficult to achieve or provide the fluidic resistance of the planar fluidic resistor portion 150 with sufficient resistance because of spatial constraints, although this depends on other factors such as the resistance of the nanopore 23, in which case the fluidic resistance of the circuit layer access hole 111 and the wafer access hole 102 become significant in the second leg 52 of the voltage divider 50.

With the dimensions of the examples discussed herein, this may start to occur once the area density of the sensors reaches 625 per mm$^2$ (corresponding to a square footprint 35 of side 40 μm).

Typically, when the area density of the sensors approaches 10,000 per mm$^2$ or more (corresponding to a square footprint 35 of side 10 μm or less), then at least one of the circuit layer access hole 111 and the wafer access hole 102 may provide a fluidic resistance in addition to the fluidic resistance of the planar fluidic resistor portion 150. The size of the layer access hole 111 and/or the wafer access hole 102 can be adjusted to provide the required fluidic resistance—if an access hole is shared between two or more sensors then the resistance is configured to be negligible.

It is desirable to increase the area density of fluidic passages 20 on the semiconductor wafer. In general, there are three main limiting factors on how densely the fluidic passages can be packed:

The configuration of the circuit components associated with each fluidic passage 20 in the circuit layer 110, which must be packaged within the footprint 35.
  The configuration of the planar fluidic resistor portion 150, which must also be packaged within the footprint 35. This problem can be mitigated by reducing the cross-sectional of the planar fluidic resistor portion 150 along its tortuous path, thereby reducing the required length thereof. It is also possible to use a multi-layer planar fluidic resistor portions 150, as will be discussed further below.

How densely the wafer access holes 102 can be packed without affecting the mechanical integrity of the semiconductor wafer.

Once the footprint of the circuit components is reduced, the limiting factor on the area density of fluidic passage 20 will shift from the circuit components to the packing of wafer access hole 102. With the dimensions of the examples discussed herein, this will start to occur once the pitch of the circuit components in the circuit layer 110 reduces significantly below 40 μm. It is also difficult to reduce the diameter of the wafer access holes 102 while still maintaining a reliable manufacturing method with a sufficiently thick wafer (e.g. 300 μm). However, the layout of the circuit components and fluidic passage 20 can be re-designed to bundle multiple fluidic passage 20 to one shared access hole. Either or both of the wafer access hole 102 and circuit layer access hole 111 may be shared. This design not only allows a further increase in the area density of fluidic passages 20 (e.g. beyond a 40 μm pitch in the examples herein), but also provides a chance to reduce the wafer access hole 102 aspect ratio requirement. Reducing the aspect ratio is advantageous when the wafer access holes 102 are manufactured using DRIE.

FIGS. 8a and 8b show two examples of base layers 100 where each access hole is shared by plural passages by being fluidically connected in common to plural planar fluidic resistor portions 150. FIG. 8a shows an example in which a single wafer access hole 102 is shared between two fluidic passages 20. FIG. 8b shows an example in which two neighbouring fluidic passages 20 share both a wafer access hole 102, and a circuit layer access hole 111. Although FIGS. 8a and 8b show two fluidic passages 20 sharing the circuit layer access hole 111 and/or the wafer access hole 102, in other embodiments more than two fluidic passages 20 may share access hole, for example three or four fluidic passages. This design can also be incorporated into the example of FIG. 7 using an SOI CMOS wafer. When a common wafer access hole 102 and/or a common circuit layer access hole 111 are implemented, their resistance can be negligible compared to the total resistance of a passage 20 to inhibit cross talk between nanopores 23 sharing a part of the passage 20 in common. The common part of the passage preferably has negligible resistance.

The cross-section of a common wafer access hole 102 can have a dimension (for example the square root of the area) that is greater than the maximum dimension (for example the square root of the area) of the sensor footprint.

In these examples, the dielectric layer 120 is between the first chamber 3 and the substrate. As an alternative the dielectric layer 120 could be between the semiconductor wafer 101 and the second chamber 4. For example, the dielectric layer 120 could be on the opposite side of the semiconductor wafer 101 from the circuit layer 110. Alternatively, the circuit layer 110 could be also formed on opposite side of the semiconductor wafer 101 to the first chamber 3, with the dielectric layer 120 formed thereon. Although this is possible, it is not preferred because it includes the capacitance of the access holes into the voltage divider thus lowered the bandwidth.

Figure 9:
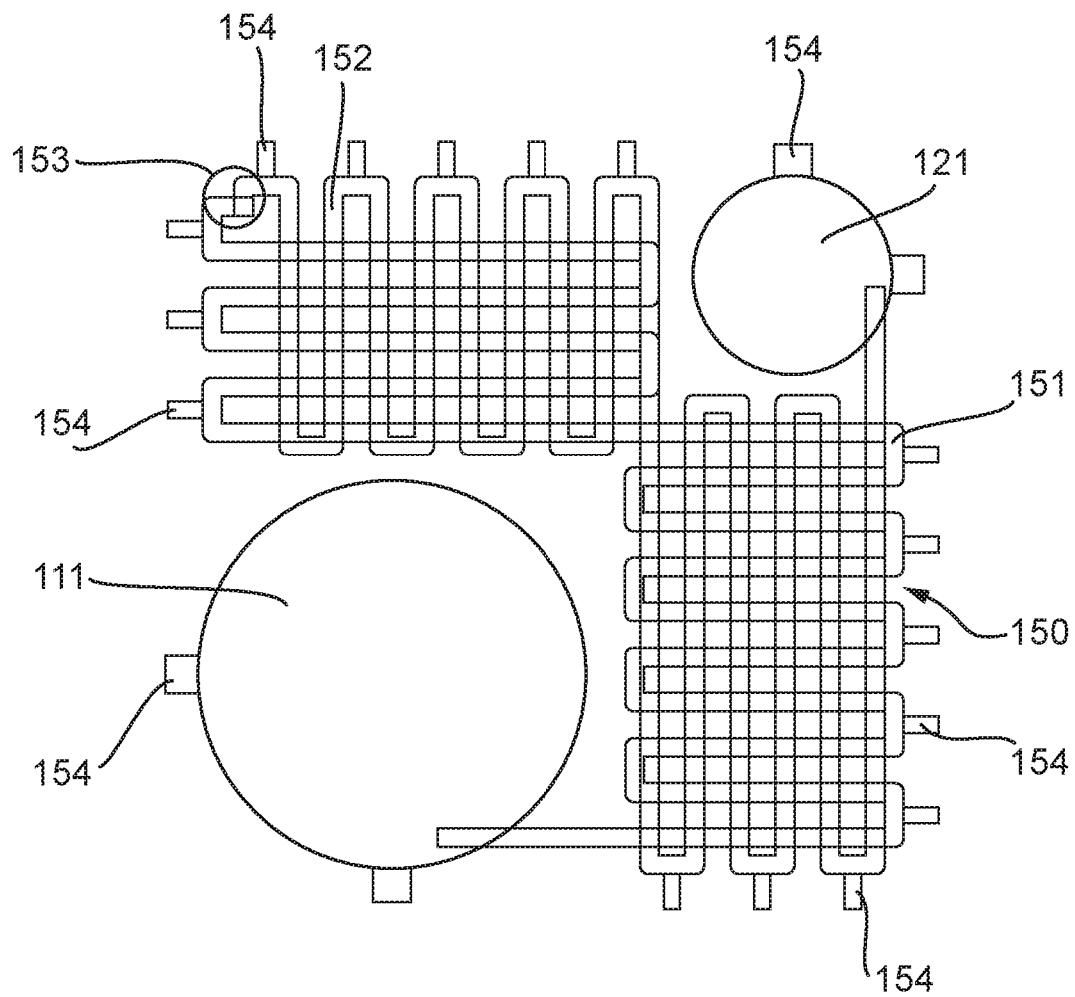
FIG. 9 is a plan view of an alternative configuration of the planar fluidic resistor portion formed in a dielectric layer of the planar structure.

The area density of fluidic passages 20 may be further increased by using a multi-layer planar fluidic resistor portion 150. FIG. 9 shows a top-down view of such a multi-layer planar fluidic resistor portion 150. In this example, the planar fluidic resistor portion 150 comprises sections 151, 152 each extending in the planar direction of the planar structure 10 but at different depths within the planar structure 10. The dielectric access hole 121 is connected to the first section 152 of the planar fluidic resistor portion 150, on top of the sensor electrode 24. In this example, the first section 152 is on top of the second section 151 (i.e. between the second section and the first chamber 3). However this is not essential, and the first section 152 could instead be below the second section 151 (i.e. between the second section 151 and the semiconductor wafer 101). The second section 151 is connected to the circuit layer access hole 111 and thereby to the wafer access hole 102. The first and second sections 152, 151 are connected together with a via 153. Vias 154 are provided adjacent parts of the passage 20 and are used for the plasma ashing process that is used to etch away the sacrificial polymer during manufacture. These vias 154 are optional, they are used to reduce the aspect ratio the ashing process has to reach inside the fluidic channel. These vias 154 are filled by the thick passivation layer following removal of the sacrificial polymer.

FIGS. 10a-10m shows a series of views of layers being processed during a method of manufacture to form a multi-layer planar fluidic resistor portion 150, which is performed as follows. FIGS. 10a to 10d show the same steps as performed in FIGS. 6a to 6d. Following these steps, sacrificial polymer has been deposited in the shape of the second section 151 of the planar fluidic resistor portion 150, and a thin passivation layer deposited on top.

Figure 10:
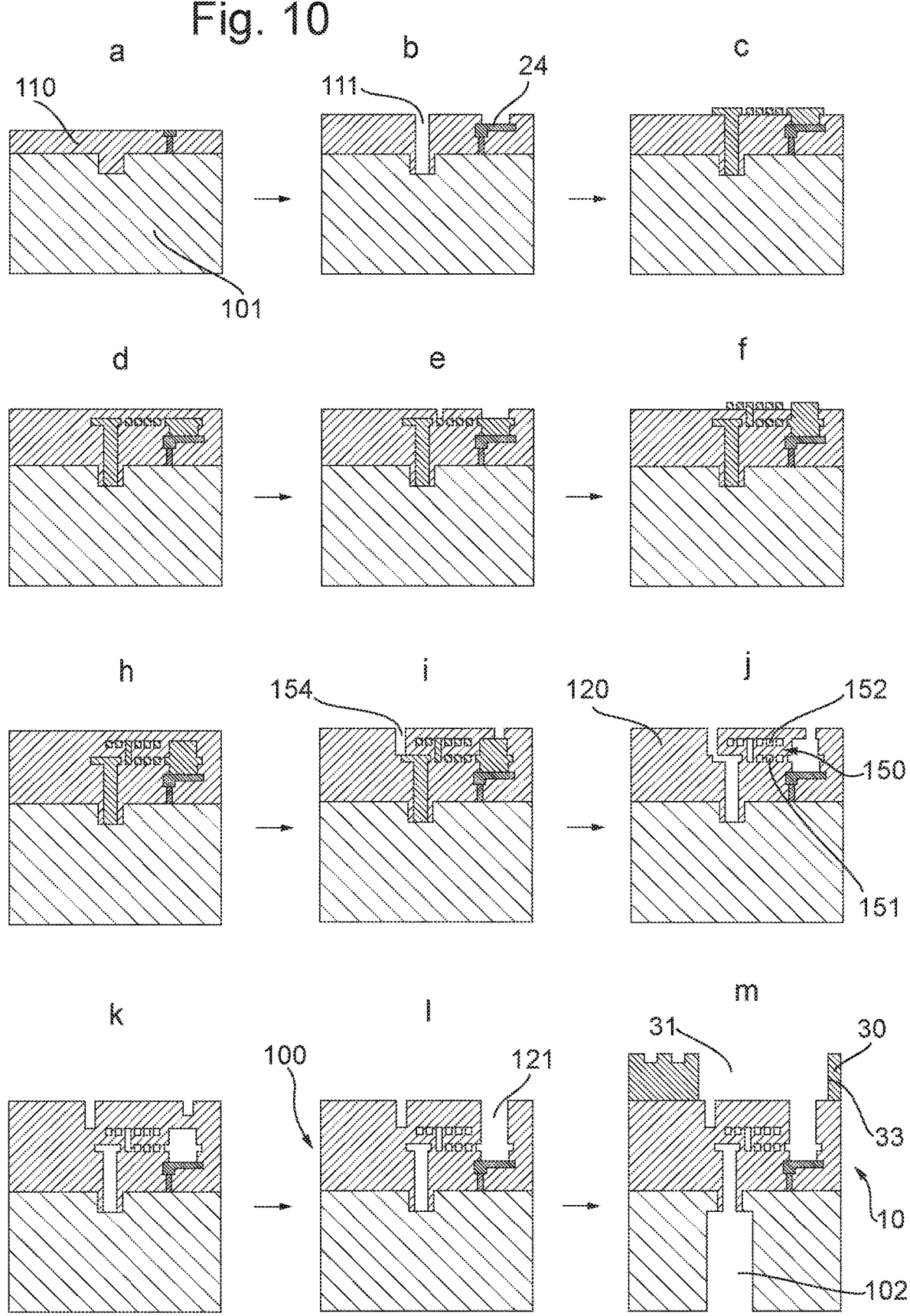
FIGS. 10a-10m are a series of cross-sectional views of layers being processed during manufacture of the planar structure in which the planar fluidic resistor portion has the alternative configuration of FIG. 9.

In FIG. 10e, the via 153 is formed in the thin passivation layer, along with a further part of the dielectric access hole 121. In FIG. 10f, further sacrificial polymer is deposited in the form of the first section 152 of the planar fluidic resistor portion 150 and the dielectric access hole 121.

In FIG. 10h, a further thin passivation layer is deposited, and in FIG. 10i, vias are formed through the further thin passivation layer and through both passivation layers to expose the sacrificial polymer in both the first and second section 152, 151 of the planar fluidic resistor portion 150, and the dielectric access hole 121. The vias expose the sides of the sacrificial polymer for the etching or plasma ashing process to remove the sacrificial polymer. FIG. 10j shows the state following the etching or plasma ashing of the sacrificial polymer.

The steps shown in FIGS. 10k to 10m are the same as those shown in FIGS. 6h to 6j, namely depositing the thick passivation layer, opening the thick passivation layer above the sensor electrode 24, and forming the wafer access hole 102.

In the examples above, the substrate which supports the dielectric layer 120 in which the planar fluidic resistor portion 150 is formed is the semiconductor wafer 101, and the planar structure 10 is formed by depositing layers directly onto the semiconductor wafer 101. However, in some embodiments, the substrate which supports a dielectric layer in which the planar fluidic resistor portion 150 is formed may be a different component from the semiconductor wafer 101 on which the circuit layer 110 is formed. In this case, the substrate which supports the planar fluidic resistor portion 150 and the semiconductor wafer 101 may be manufactured separately and then bonded together.

An example of a method of making a base layer 100 of a planar structure 10 of this type is shown in FIGS. 11a-11e and performed as follows. In this example, the substrate on which the planar fluidic resistor portion 150 is formed is a MEMS (micro-electromechanical system) wafer 170. The MEMS wafer 170 and has the advantage of being able to withstand a high temperature thermal oxide process used for forming the planar fluidic resistor portion 150 and allows conventional MEMS processes to be used. The MEMS wafer 170 may be made of any suitable material, for example quartz, silicon oxide, glass, aluminium oxide or sapphire. In 10 principle, the MEMS wafer 170 could be replaced by a substrate made from any other material suitable for supporting the dielectric layer 172 described below, for example being a semiconductor wafer.

Figure 11:
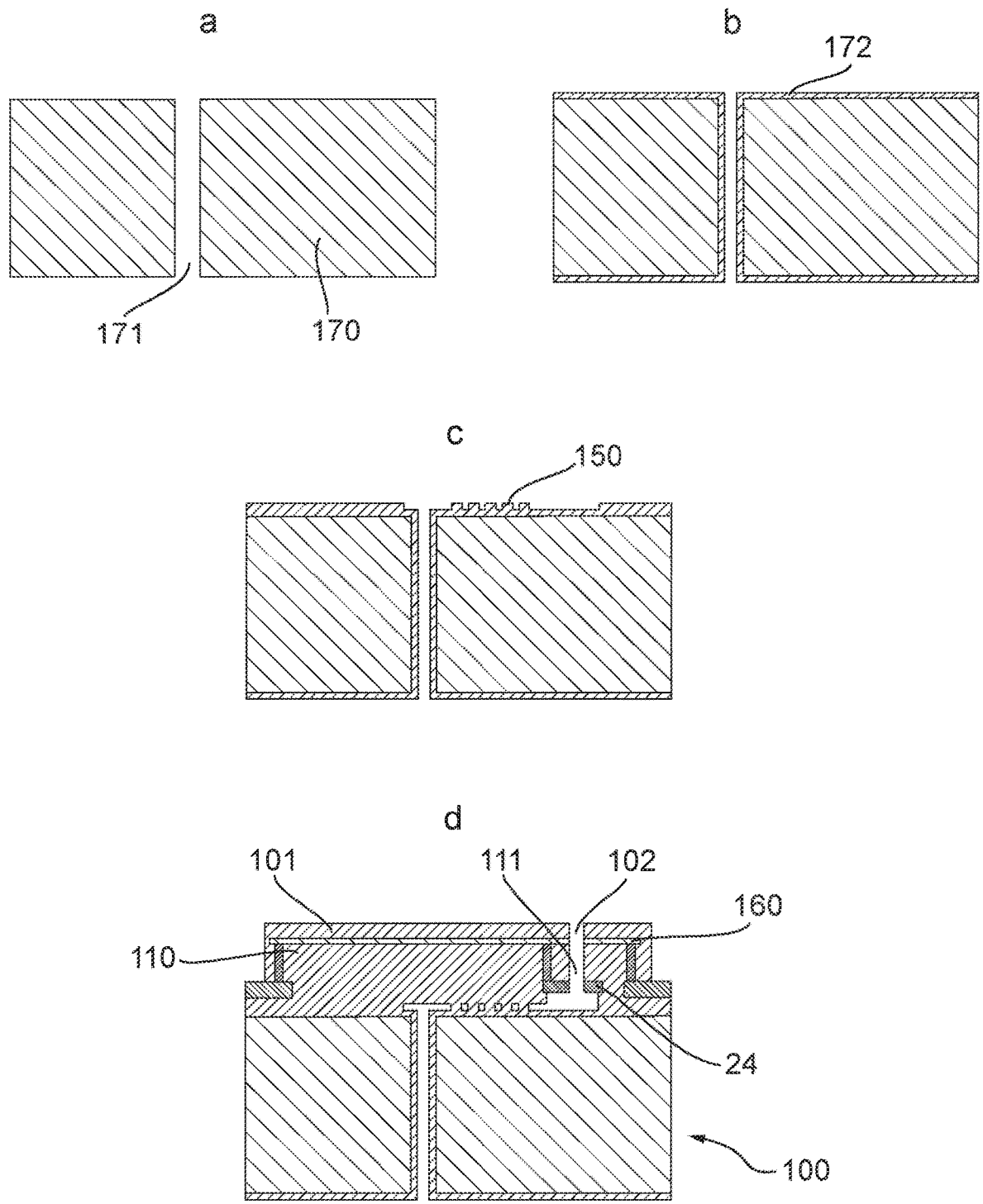
FIGS. 11a-11d are a series of cross-sectional views of layers being processed during manufacture of the base layer of the planar structure with a fourth modified construction in which the planar fluidic resistor portion is formed on a substrate that is bonded to semiconductor wafer.

As shown in FIG. 11a, the MEMS wafer 170 is provided and a MEMS wafer access hole 171 is formed extending therethrough by DRIE.

FIG. 11b shows the formation of a dielectric layer 172 on the surface of the MEMS wafer 170 by thermal oxidation. Typically, the dielectric layer 172 may have thickness of order 2 μm or more. Thus, in this example, the dielectric layer 172 is an oxide of the material of the MEMS wafer 170.

FIG. 11c shows the formation of the planar fluidic resistor portion 150 in the dielectric layer 172 by etching using a lithographic process. The planar fluidic resistor portion 150 may have a form as described above.

In FIG. 11d, the base layer 100 is formed by bonding the MEMS wafer 170 shown in FIG. 11c to a semiconductor wafer 101 supporting a circuit layer 110. The semiconductor wafer 101 has the same construction as described above except that the dielectric layer 120 is not provided and the semiconductor wafer 101 is upside down in FIG. 11d compared to the previous figures. As described above, the circuit layer 110 comprises circuit components connected to the sensor electrode 24. The semiconductor wafer 101 and the circuit layer 110 are provided with access holes 102, 111 which extend therethrough and form part of the passages 20. In this example, the semiconductor wafer 101 is an SOI CMOS wafer including an insulator layer 170, similar to that shown in FIG. 7, and the handle layer is removed after bonding.

Similarly, the semiconductor wafer 101 and circuit layer 101 may be manufactured using the same processes as described above.

The MEMS wafer 170 shown in FIG. 11c is bonded to the semiconductor wafer 101 by bonding the outer surface of the dielectric layer 172 in which the planar fluidic resistor portion 150 is formed to the outer surface of the circuit layer 110. As a result, the MEMS wafer 170, which forms the substrate in this example, is bonded to the semiconductor wafer 101 between the semiconductor wafer 101 and the second chamber 4.

As in the above examples, the nanopore support layer 30 is fixed to the base layer 100 shown in FIG. 11d, for example by forming the nanopore support layer 30 separately and bonding it to the base layer 100, or forming the nanopore support layer 30 directly on the base layer 100.

This bonded two wafer route for fabrication, with separate wafers used to form the planar fluidic resistor portion 150 and the circuit components has the advantage that the processing for forming each structure can be optimised more easily when performed separately. For example, the semiconductor wafer 101 can be thinned down prior to forming the wafer access holes 102 more easily without the layers forming the planar fluidic resistor portion 150 thereon. This may advantageous in some situations. However, the two-wafer process adds considerable complexity, since two entirely separate fabrication processes must be carried out, and an additional joining step performed. The processes used to process the SOI CMOS also creates limitations on circuit design and foundry choices. This is likely to increase the cost of manufacture compared to forming all of the planar structure 10 in a single, albeit longer, process. Therefore, the single wafer method is likely to be preferred in many situations.

Although various methods for manufacturing the planar structure have been discussed above, the planar structure is not limited to these methods, and may be formed by any other suitable method.

In the examples above, the planar fluidic resistor portion 150 is formed in a dielectric layer, for example the dielectric layer 120 supported by the semiconductor wafer 101 in FIG. 2 or the dielectric layer 172 supported by the MEMS wafer 170 in FIGS. 11a-11d. As an alternative, the planar fluidic resistor portion 150 may be formed in the nanopore support layer 30. This provides the advantage that the planar fluidic resistor portion 150 may be manufactured using the same processes used to manufacture the structure of nanopore support layer 30. In the following method, the planar fluidic resistor portion 150 follows a tortuous path that may be the same as that shown in FIG. 5, albeit that it is formed in the nanopore support layer 30.

An example of a method of making a planar structure 10 of this type is shown in FIGS. 12a-12f and performed as follows.

FIGS. 11a and 12b are in general terms the same as the steps described above with respect to FIGS. 6a and 6b.

After these steps, the semiconductor wafer 101 (which forms the substrate of the planar structure 10) and circuit layer 110 are present, with the sensor electrode 24 deposited. A passivation layer has been deposited, and the circuit layer access hole 111 opened through the passivation layer and circuit layer 110. FIG. 12c shows the formation of the wafer access hole 102 prior to formation of the planar fluidic resistor portion 150. This is in contrast to the method of FIG. 6, where the wafer access hole 102 is only formed in the penultimate step after the formation of the planar fluidic resistor portion 150. Alternatively, the wafer access hole 102 can be formed after the nanopore support layer 30 has been formed.

FIG. 12d shows a sacrificial polymer layer 180 deposited in the shape of the planar fluidic resistor portion 150 on top of the dielectric layer 110. This is similar to the step shown in FIG. 6c. The sacrificial polymer layer 180 may comprise photoresist, which can be deposited by spin coating and/or lamination, and subsequently patterned into the shape of the planar fluidic resistor portion 150. The patterning of the photoresist may, for example, comprise exposure using a mask and subsequent development.

As shown in FIG. 12e, a photoresist layer 181 is then deposited onto the base layer 100, covering the sacrificial polymer layer 180. The photoresist layer 181 is used to form the nanopore support structure 30. The photoresist layer 181 is exposed to light and developed so as to form the wall layer 32 comprising walls 33 that define the wells 31.

As shown in FIG. 12f, the photoresist layer 181 is then developed, and the sacrificial polymer layer 180 is also removed to form the planar fluidic resistor portion 150.

Following these steps, and similarly to the embodiments described above, the planar structure comprises the substrate, which in this example comprises a semiconductor wafer 101, the circuit layer 110 supported by the semiconductor wafer 101, the circuit layer comprising circuit components connected to the sensor electrode, and the nanopore support layer 30 that is 30 configured to support the nanopores 23 in the membranes 22 extending across the passages 20. However, in contrast to the embodiments above, the planar fluidic resistor portions 150 are formed in the nanopore support layer 30.

As shown in FIG. 12f, the nanopore support layer 30 is provided with wells 31. When the planar structure 10 is integrated into the nanopore sensing device 1, the wells 31 open into the first chamber 3. The wells 31 form part of the passages 20 and are configured to support the nanopores 23 in the membranes 22 extending across the wells 31.

In the nanopore sensing device 1, the first and second chambers 3, 4 are on opposite sides of the planar structure 10. The passages 20 extend through the planar structure 10 and the substrate (in this case the semiconductor wafer 101) is provided with access holes 102 which extend therethrough and form part of the passages 20.

As illustrated in FIG. 8, in some embodiments, each access hole 102 is shared by plural passages 20 by being fluidically connected in common to plural planar fluidic resistor portions 150. In the case of the planar structure of FIG. 12, where the planar fluidic resistor portions 150 are formed in the nanopore support layer 30, the plural passages 20 may be connected to one another within the nanopore support layer 30, or alternatively may be connected by sharing only of the wafer access hole 102 and/or the circuit layer access hole 111 in the base layer 100.

Table 1 sets out some non-limitative examples of area densities of the sensors in the nanopore sensing device 1 which may be applied to any of the configurations described above. Table 1 also sets out the corresponding sizes and areas of the footprints 35 in the case that the footprints 35 are square, although the footprints 35 could have any other shape.

TABLE 1

| Area density (no. per mm²) | Size of footprint 35 (μm) | Area of footprint 35 (μm²) |
|---|---|---|
| 100 | 100 | 10000 |
| 400 | 50 | 2500 |
| 625 | 40 | 1600 |
| 2500 | 20 | 400 |
| 10000 | 10 | 100 |
| 40000 | 5 | 25 |
| 62500 | 4 | 16 |
| 250000 | 2 | 4 |
| 1000000 | 1 | 1 |

Table 2 sets out some non-limitative examples of distribution of fluidic resistance between the nanopore 23 and different parts of the passage 20 for different area densities of sensor that may be applied to the nanopore sensing device 1 in the configurations described above.

Figure 12:
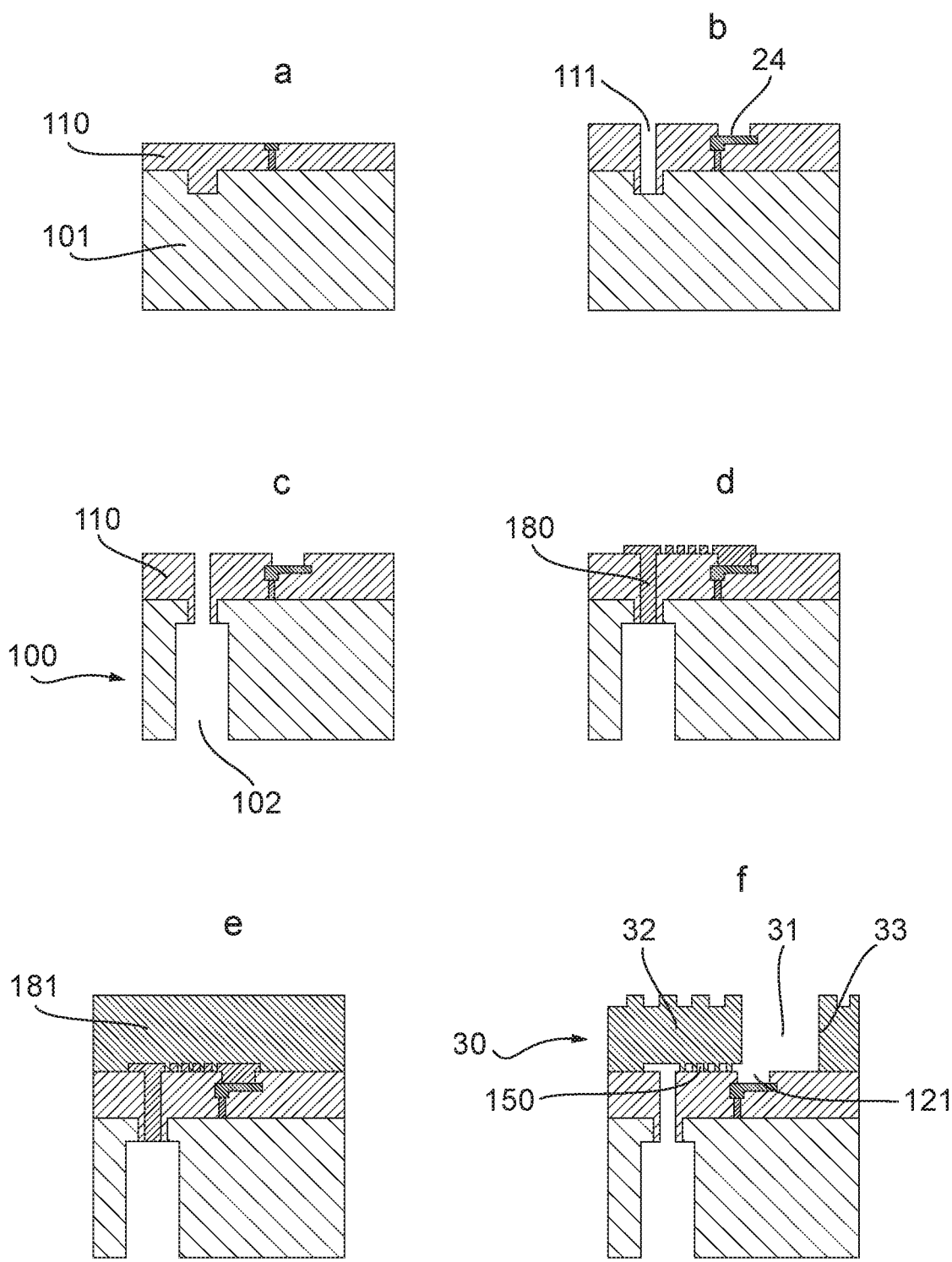
FIGS. 12a-12f are a series of cross-sectional views of layers being processed during manufacture of the planar structure with a fifth modified construction in which the planar fluidic resistor portion is formed in the nanopore support layer.

In Table 2:
- the column labelled "23" indicates the % of the fluidic resistance provided by the nanopore 23;
- the column labelled "30" indicates the % of the fluidic resistance provided by a planar fluidic resistor portion 150 formed in the nanopore support layer 30, for example as shown in FIG. 12;
- the column labelled "120-above" indicates the % of the fluidic resistance provided by a planar fluidic resistor portion 150 formed in a dielectric layer 120 disposed above the circuit layer 110, for example as shown in FIG. 2;
- the column labelled "120-below" indicates the % of the fluidic resistance provided by a planar fluidic resistor portion 150 formed in a dielectric layer 120 disposed between the circuit layer 110 and the semiconductor wafer 101, in accordance with the alternative described above;
- the column labelled "111" indicates the % of the fluidic resistance provided by the dielectric access hole 111;
- the column labelled "102" indicates the % of the fluidic resistance provided by the wafer access hole 102 (and/or the circuit layer access hole 111) in the case that each passage 20 has a respective wafer access hole 102, for example as shown in FIG. 2; and
- the column labelled "102-common" indicates the % of the fluidic resistance provided by the wafer access hole 102 (and/or the circuit layer access hole 111) in the case that plural passages 20 share a wafer access hole 102 (and/or the circuit layer access hole 111), for example as shown in FIGS. 8a and 8b. NB: when a common wafer access hole 102 and/or a common circuit layer access hole 111 are implemented, their resistance can be negligible compared to the total resistance to inhibit cross talk between nanopores 23 sharing apart of the passage 20 in common. Common parts of the passages 20 preferably have negligible resistance.

TABLE 2

| Area density (no. per mm²) | 23 | 30 | 120-above | 120-below | 111 | 102 | 102-common |
|---|---|---|---|---|---|---|---|
| 100 | 50% | 50% | | | | | |
| 100 | 50% | | 50% | | | | |
| 100 | 50% | | | 50% | | | |
| 100 | 50% | | | | 50% | | |
| 100 | 50% | | | | | 50% | |
| 100 | 90% | | | | 10% | | |
| 100 | 90% | | | 10% | | | |
| 100 | 90% | | 10% | | | | |
| 100 | 90% | 10% | | | | | |
| 10000 | 50% | 25% | 25% | | | | 0% |
| 10000 | 50% | 25% | | 25% | | | 0% |
| 10000 | 50% | | | 25% | 25% | | |
| 10000 | 50% | 25% | | | | 25% | |
| 10000 | 90% | 5% | 5% | | | | 0% |
| 10000 | 90% | 5% | | 5% | | | 0% |
| 10000 | 90% | | | 5% | | 5% | |
| 10000 | 90% | 5% | | | | 5% | |
| 25000 | 50% | 20% | 20% | | 10% | | 0% |
| 25000 | 90% | 4% | 3% | | 3% | | 0% |
| 25000 | 90% | 4% | | 4% | 2% | | 0% |
| 25000 | 80% | 20% | | 5% | 5% | | 0% |
| 25000 | 70% | 30% | | 10% | 10% | | 0% |

Some general points are as follows.

The ratio of the percentage "%" in the column labelled "23", which indicate the % of the fluidic resistance provided by the nanopore 23, to the total resistance in all other columns can be 1:1. This ratio can range from 1:1 up to around 99:1. The upper range of the ratio can be for example 3:2, 7:3, 4:1 or 19:1. An exemplary ratio is 9:1. In other words, the nanopore resistance can be ~50% when the ratio is 1:1 and can be >50% as the resistance of the nanopore dominates the total resistance in the passage. The nanopore resistance can be >60%, >70% . . . >90% . . . etc.

The present inventors have found that whilst a nanopore resistance of around 1:1 provides an optimal signal:noise ratio, it results in an increased voltage drop across the nanopore leading to increased ion depletion during translocation and measurement of a species such as DNA through a nanopore. This results in a change in the fluidic and nanopore resistance, eventually leading to a reduction of the voltage signal. Thus a nanopore resistance of greater than 50% of the total resistance is preferred. A nanopore resistance of ~90% will cause ~20 mV voltage drop, which is considered an acceptable upper bound for the voltage drop while allowing the generation of enough voltage signal on the sensing electrode.

As the density area density of the array increased beyond a certain number of sensors per mm², such as densities above 10000 per mm² and at densities of 25000 per mm² and above the resistance of the fluidic passage is distributed between planar fluidic resistance portions and access hole portions, along its length. It is to be noted that at high densities the wafer access hole can be common to two or more sensors, and when this occurs the resistance of a common access hole is preferably negligible to inhibit detectable cross talk between nanopore sensors that share the same wafer access hole.

The nanopore sensing device 1 shown in FIGS. 1 and 2 is filled with fluid and the membranes 22 are shown extending across the respective passages 20 and the nanopores 23 inserted in the membranes 22, but some types of nanopore sensing device 1 may be provided without the membranes 22 and nanopores 23. In that case, the end user of the nanopore sensing device 1 carries out the steps to form the membranes 22 and cause the nanopores 23 to insert therein.

WO 2020/183172 discloses various nanopore sensing devices, and the structures and methods disclosed in WO 2020/183172 may be also applied to the present disclosure. WO 2020/183172 is incorporated by reference herein in its entirety.

Examples of the membranes 22 and the nanopores 23 are as follows.

In one type of nanopore sensing device 1, the nanopores 23 are biological nanopores and the membranes 22 are capable of having the biological nanopores 23 inserted therein. In another type of nanopore sensing device 1, the membranes 22 are solid state layers and the nanopores 23 are formed therein either as apertures or as biological nanopores.

The membrane 22 may be an amphiphilic layer, that is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). The membrane 22 may be a triblock or diblock copolymer membrane.

Membranes 22 formed from block copolymers hold several advantages over biological lipid membranes. Because the triblock copolymer is synthesized, the exact construction can be carefully controlled to provide the correct chain lengths and properties required to form membranes and to interact with pores and other proteins.

The membrane 22 can be one of the membranes disclosed in WO2014/064443 or WO2014/064444, hereby incorporated by reference in their entirety. These documents also disclose suitable polymers.

The amphiphilic molecules may be chemically modified or functionalized to facilitate coupling of the polynucleotide.

The amphiphilic layer may be a monolayer or a bilayer.

The membrane 22 may be a lipid bilayer. Suitable lipid bilayers are disclosed in WO2008/102121, WO2009/077734 and WO2006/100484, hereby incorporated by reference in their entirety. Methods for forming lipid bilayers are known in the art. Lipid bilayers are commonly formed by the method of Montal and Mueller (Proc. Natl. Acad. Sci. USA., 1972; 69: 3561-3566).

The membrane 22 may be a solid-state layer. Suitable state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid-state layer may be formed from graphene. Suitable graphene layers are disclosed in WO2009/035647, hereby incorporated by reference in its entirety. Yusko et al., Nature Nanotechnology, 2011; 6: 253-260 and US Patent Application No. 2013/0048499, hereby incorporated by reference in their entirety, describe the delivery of proteins to transmembrane pores in solid state layers without the use of microparticles.

The nanopore 23 may be any transmembrane pore. The nanopore 23 may be biological or artificial. Suitable nanopores 23 include, but are not limited to, protein pores, polynucleotide pores and solid-state pores. The nanopore 23 may be a DNA origami pore (Langecker et al., Science, 2012; 338: 932-936).

The transmembrane protein pore may comprise a barrel or channel through which the ions may flow. The barrel or channel of the transmembrane protein pore typically comprises amino acids that facilitate interaction with nucleotides, polynucleotides or nucleic acids.

Transmembrane protein pores for use in accordance with the invention can be derived from}-barrel pores or α-helix bundle pores. The transmembrane pore may be derived from or based on, for example, Msp, α-hemolysin (α-HL), lysenin, CsgG, ClyA, Sp1 and hemolytic protein fragaceatoxin C (FraC). The transmembrane protein pore can be derived from CsgG. Suitable pores derived from CsgG are disclosed in WO 2016/034591. The transmembrane pore may be derived from lysenin. Suitable pores derived from lysenin are disclosed in WO 2013/153359.

The analytes (including, e.g., proteins, peptides, small molecules, polypeptide, polynucleotides) may be present in an analyte. The analyte may be any suitable sample. The analyte may be a biological sample. Any embodiment of the methods described herein may be carried out in vitro on an analyte obtained from or extracted from any organism or microorganism. The organism or microorganism is typically archaean, prokaryotic or eukaryotic and typically belongs to one of the five kingdoms: plantae, animalia, fungi, monera and protista. In some embodiments, the methods of various aspects described herein may be carried out in vitro on an analyte obtained from or extracted from any virus.

The analyte can be a fluid sample. The analyte can comprise a body fluid. The body fluid may be obtained from a human or animal. The human or animal may have, be suspected of having or be at risk of a disease. The analyte may be urine, lymph, saliva, mucus, seminal fluid or amniotic fluid, but can be whole blood, plasma or serum. Typically, the analyte is human in origin, but alternatively it may be from another mammal such as from commercially farmed animals such as horses, cattle, sheep or pigs or may alternatively be pets such as cats or dogs. Alternatively, an analyte can be of plant origin.

The analyte may be a non-biological sample. The non-biological sample can be a fluid sample. An ionic salt such as potassium chloride may be added to the sample to effect ion flow through the nanopore.

The polynucleotide may be single stranded or double stranded. At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art. The polynucleotide can be naturally occurring or artificial.

The method may involve measuring two, three, four or five or more characteristics of a polynucleotide. The one or more characteristics can be selected from (i) the length of the polynucleotide, (ii) the identity of the polynucleotide, (iii) the sequence of the polynucleotide, (iv) the secondary structure of the polynucleotide and (v) whether or not the polynucleotide is modified.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 15 2010; 132(50):17961-72, and International Application WO 2000/28312.

The secondary structure may be measured in a variety of ways. For instance, if the method involves an electrical measurement, the secondary structure may be measured using a change in dwell time or a change in ion current flowing through the pore. This allows regions of single-stranded and double-stranded polynucleotide to be distinguished.

The presence or absence of any modification may be measured. The method can comprises determining whether or not the polynucleotide is modified by methylation, by oxidation, by damage, with one or more proteins or with one or more labels, tags or spacers. Specific modifications will result in specific interactions with the pore which can be measured using the methods described below.

In some embodiments of various aspects described herein, the method may involve further characterizing the target polynucleotide. As the target polynucleotide is contacted with the pore, one or more measurements which are indicative of one or more characteristics of the target polynucleotide are taken as the polynucleotide moves with respect to the pore.

The method may involve determining whether or not the polynucleotide is modified. The presence or absence of any modification may be measured. The method can comprises determining whether or not the polynucleotide is modified by methylation, by oxidation, by damage, with one or more proteins or with one or more labels, tags or spacers.

Also provided is an apparatus for characterising a target analyte, such as a target polynucleotide. The apparatus comprises a plurality of the pores as disclosed herein and a plurality of membranes. The plurality of pores can be present in the plurality of membranes. The number of pores and membranes can be equal. A single pore can be present in each membrane.

The apparatus for characterising target analytes, may comprise or an array of pores as disclosed herein, in a plurality of membranes.

The apparatus can further comprise instructions for carrying out the method. The apparatus may be any conventional apparatus for analyte analysis, such as an array or a chip. Any of the embodiments discussed above with reference to the methods are equally applicable to the apparatus of the invention.

The apparatus can be set up to carry out a method as disclosed herein.

The apparatus can comprise: a nanopore sensor device 1 that is capable of supporting the plurality of pores and membranes and being operable to perform analyte characterisation using the pores and membranes; and at least one port for delivery of the material for performing the characterisation.

Alternatively, the apparatus can comprise: a nanopore sensor device 1 that is capable of supporting the plurality of pores and membranes being operable to perform analyte characterisation using the pores and membranes; and at least one reservoir for holding material for performing the characterisation.

The apparatus can comprise: a sensor device that is capable of supporting the membrane and plurality of pores and membranes and being operable to perform analyte characterising using the pores and membranes; at least one reservoir for holding material for performing the characterising; a fluidics system configured to controllably supply material from the at least one reservoir to the sensor device; and one or more containers for receiving respective samples, the fluidics system being configured to supply the analytes selectively from one or more containers to the sensor device.

The apparatus may be any of those described in WO 2009/077734, WO 2010/122293, WO 2011/067559 or WO 00/28312, modified to include the nanopore sensing device 1 disclosed herein.

Control of the movement of an analyte with respect to the nanopore e.g. speed of translocation, rejection of the analyte etc, can be managed by the systems and methods disclosed in WO2016/059427. Rejection of an analyte by the nanopore sensor can comprise ejection of the analyte from the nanopore.

The features in description above and drawings are interchangeable and compatible in light of the teaching herein. The present invention has been described above purely by way of example, and modifications can be made within the spirit and scope of the invention, which extends to equivalents of the features described and combinations of one or more features described herein. The invention also consists in any individual features described or implicit herein.

The invention claimed is:

1. A nanopore sensing device comprising:
   first and second chambers;
   a planar structure provided with plural fluidic passages extending between the first and second chambers, the planar structure being configured to support nanopores in membranes across respective passages; and
   sensor electrodes arranged to sense a fluidic electrical potential in respective passages between the nanopores and the second chamber,
   wherein the passages comprise planar fluidic resistor portions between the sensor electrode and the second chamber, the planar fluidic resistor portions extending in a planar direction of the planar structure and being configured to form a fluidic resistor; and
   wherein the resistance of each nanopore is greater than 50% of the total resistance of the corresponding passage.

2. A nanopore sensing device according to claim 1, wherein the planar structure comprises:
   a nanopore support layer that is configured to support the nanopores in the membranes extending across the passages; and
   a further layer, the planar fluidic resistor portions being formed in the further layer.

3. A nanopore sensing device according to claim 2, wherein the nanopore support layer is provided with wells opening into the first chamber, the wells forming part of the passages and being configured to support said nanopores in said membranes extending across the wells.

4. A nanopore sensing device according to claim 2, wherein the further layer is a dielectric layer.

5. A nanopore sensing device according to claim 2, wherein the planar structure further comprises a substrate, the further layer being supported by the substrate.

6. A nanopore sensing device according to claim 5, wherein the first and second chambers are on opposite sides of the planar structure, the passages extend through the planar structure and the substrate is provided with access holes which extend therethrough and form part of the passages.

7. A nanopore sensing device according to claim 1, wherein
the first and second chambers are on opposite sides of the planar structure, the passages extending through the planar structure, and
the planar structure comprises:
a substrate; and
a further layer, the further layer being supported by the substrate,
wherein the planar fluidic resistor portions are formed in the further layer, and the substrate is provided with access holes extending therethrough, the access holes forming part of the passages.

8. A nanopore sensing device according to claim 7, wherein the planar structure further comprises a nanopore support layer that is configured to support the nanopores in the membranes extending across the passages.

9. A nanopore sensing device according to claim 8, wherein the nanopore support layer is provided with wells opening into the first chamber, the wells forming part of the passages and being configured to support the nanopores in the membranes extending across the wells.

10. A nanopore sensing device according to claim 7, wherein the further layer is a dielectric layer.

11. A nanopore sensing device according to claim 6, wherein the further layer is between the first chamber and the substrate.

12. A nanopore sensing device according to claim 6, wherein each access hole is shared by plural passages by being fluidically connected in common to plural planar fluidic resistor portions.

13. A nanopore sensing device according to claim 5, wherein the substrate is a semiconductor wafer.

14. A nanopore sensing device according to claim 13, wherein the planar structure further comprises a circuit layer supported by the semiconductor wafer, the circuit layer comprising circuit components connected to the sensor electrode.

15. A nanopore sensing device according to claim 14, wherein the circuit layer is formed on the semiconductor wafer and the dielectric layer is formed on the circuit layer.

16. A nanopore sensing device according to claim 6, wherein
the planar structure further comprises a semiconductor wafer having a circuit layer supported thereby, the circuit layer comprising circuit components connected to the sensor electrode, the semiconductor wafer and the circuit layer is provided with access holes which extend therethrough and form part of the passages, and the substrate is bonded to the semiconductor wafer between the semiconductor wafer and the second chamber.

17. A nanopore sensing device according to claim 1, wherein the planar structure comprises:
a substrate;
a circuit layer supported by the substrate, the circuit layer comprising circuit components connected to the sensor electrode; and
a nanopore support layer that is configured to support the nanopores in the membranes extending across the passages, the planar fluidic resistor portions being formed in the nanopore support layer.

18. A nanopore sensing device according to claim 17, wherein the nanopore support layer is provided with wells opening into the first chamber, the wells forming part of the passages and being configured to support said nanopores in said membranes extending across the wells.

19. A nanopore sensing device according to claim 17, wherein the first and second chambers are on opposite sides of the planar structure, the passages extend through the planar structure and the substrate is provided with access holes which extend therethrough and form part of the passages.

20. A nanopore sensing device according to claim 19, wherein each access hole is shared by plural passages by being fluidically connected in common to plural planar fluidic resistor portions.

21. A nanopore sensing device according to claim 17, wherein the substrate is a semiconductor wafer.

22. A nanopore sensing device according to claim 1, wherein the planar fluidic resistor portion extends along a tortuous path.

23. A nanopore sensing device according to claim 1, wherein the nanopores are biological nanopores and the membranes are capable of having the biological nanopores inserted therein.

24. A nanopore sensing device according to claim 23, wherein the planar structure further comprises the membranes extending across the respective passages and optionally also the biological nanopores inserted in the membranes.

25. A nanopore sensing device according to claim 1, wherein the membranes are solid state membranes, the planar structure further comprises the solid-state membranes and the nanopores are formed therein.

26. A nanopore sensing device according to claim 1, wherein the planar fluidic resistor portion comprises sections each extending in the planar direction of the planar structure but at different depths within the planar structure.

27. A nanopore sensing device according to claim 1, wherein the passages comprise wells opening into the first chamber, the planar structure being configured to support the nanopores in membranes extending across the wells.

28. A nanopore sensing device according to claim 1, wherein the first and second chambers are on opposite sides of the planar structure and the passages extend through the planar structure.

29. A nanopore sensing device according to claim 1, further comprising drive electrodes in the first and second chambers.

30. A nanopore sensing device according to claim 1, wherein the resistance of each nanopore is 90% of the total resistance of the corresponding passage.

* * * * *